US008012411B1

(12) United States Patent
Betty et al.

(10) Patent No.: US 8,012,411 B1

(45) Date of Patent: *Sep. 6, 2011

(54) ENHANCED TOXIC CLOUD KNOCKDOWN SPRAY SYSTEM FOR DECONTAMINATION APPLICATIONS

(75) Inventors: Rita G. Betty, Rio Rancho, NM (US); Mark D. Tucker, Albuquerque, NM (US); John E. Brockmann, Albuquerque, NM (US); Daniel A. Lucero, Albuquerque, NM (US); Bruce L. Levin, Tijeras, NM (US); Jonathan Leonard, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 689 days.

This patent is subject to a terminal disclaimer.

(21) Appl. No.: 11/673,835

(22) Filed: Feb. 12, 2007

Related U.S. Application Data

(60) Provisional application No. 60/772,760, filed on Feb. 13, 2006, provisional application No. 60/842,826, filed on Sep. 7, 2006.

(51) Int. Cl.
*A61L 9/00* (2006.01)

(52) U.S. Cl. ............................................ 422/4; 422/306

(58) Field of Classification Search ................ 422/4, 88, 422/306

See application file for complete search history.

(56) References Cited

U.S. PATENT DOCUMENTS

| | | | | | |
|---|---|---|---|---|---|
| 5,902,619 | A * | 5/1999 | Rubow et al. | ................. | 426/235 |
| 6,465,409 | B1 * | 10/2002 | Carr et al. | ...................... | 510/382 |
| 6,566,574 | B1 | 5/2003 | Tadros et al. | | |
| 6,803,034 | B2 * | 10/2004 | DuVal et al. | ................. | 424/76.2 |
| 2002/0021985 | A1 * | 2/2002 | Peterson et al. | ................. | 422/88 |
| 2004/0022867 | A1 * | 2/2004 | Tucker et al. | ................. | 424/616 |

OTHER PUBLICATIONS

John E. Brockmann, Removal of Sarin Aerosol and Vapor by Wate Sprays, SAND98-1890, Unlimited Release, Printed Sep. 1998.

Sedward Law, Embedded-Electrode-Induction Spray-Charging Nozzle: Theoretical and Engineering Design, . . . Transactions of the ASAE—1978.

S. Edward Law, Steven C. Cooper & Mark A. Harrison, Electrostatic Spray Application of Decontaminant . . . , Inst. Phys Conf. Ser. No. 178: 2003 10P Publishing, Ltd.

ESS, Electrostatic Sprayers for Grape Growers, 2002 ESS, Inc., Publications date Jan. 1, 2007.

Scott M. Russell, Sanitizing Poultry Processing Facilities Using Electrostatic Spraying, Univ. of Georgia, Pub. date Jan. 1, 2004.

* cited by examiner

*Primary Examiner* — Kevin C Joyner

(74) *Attorney, Agent, or Firm* — Olivia J. Tsai

(57) ABSTRACT

Methods and systems for knockdown and neutralization of toxic clouds of aerosolized chemical or biological warfare (CBW) agents and toxic industrial chemicals using a non-toxic, non-corrosive aqueous decontamination formulation.

31 Claims, 5 Drawing Sheets

ENHANCED TOXIC CLOUD KNOCKDOWN SPRAY SYSTEM FOR DECONTAMINATION APPLICATIONS

CROSS-REFERENCE TO RELATED APPLICATIONS

This application is related to U.S. patent application Ser. No. 10/251,569 filed on Sep. 20, 2002 now U.S. Pat. No. 7,390,432; application Ser. No. 10/974,222 filed Oct. 27, 2004 now U.S. Pat. No. 7,514,493; application Ser. No. 10/623,370 filed Jul. 18, 2003 now U.S. Pat. No. 7,282,470; application Ser. No. 10/740,317 filed Dec. 18, 2003 now U.S. Pat. No. 7,276,468; application Ser. No. 10/850,802 filed May 21, 2004 now U.S. Pat. No. 7,125,497; application Ser. No. 10/765,678 filed Jan. 27, 2004 now U.S. Pat. No. 7,271, 137; and application Ser. No. 11/341,678 filed Jan. 27, 2006 now U.S. Pat. No. 7,755,480; and the specifications thereof is incorporated herein by reference.

This application claims the benefit of U.S. Provisional Patent Application Ser. No. 60/772,760 filed on Feb. 13, 2006, and U.S. Provisional Patent Application Ser. No. 60/842,826 filed Sep. 7, 2006, the specifications thereof are incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates generally to methods and systems for knockdown and neutralization of toxic clouds of aerosolized chemical or biological warfare (CBW) agents and toxic industrial chemicals using an aqueous decontamination formulation.

Toxic clouds of aerosolized toxic materials can be released by a terrorist attack, or an industrial accident. Methods and systems are needed to rapidly and effectively neutralize the toxic material and render the cloud harmless; thereby saving lives and minimizing impact to infrastructure. Successful knockdown and decontamination of the toxic cloud is a critical goal for both hazmat responders and critical military operations, preferably while the toxic material is still aerosolized.

Toxic clouds can be released in outdoor areas, for example: at industrial sites where accidental chemical spills may occur (train derailment, factories, shipping ports); at open public venues such as outdoor sports stadiums; or indoors (such as subway tunnels or shopping malls). Toxic clouds may also be released from breach of nuclear reactor containment, or during de-militarization of chemical weapons, explosives or other hazardous materials.

Liquid drops of the decontamination fluid falling through a toxic cloud will mechanically scavenge particles and vapors as they fall. The efficiency with which toxic particles and vapors are removed depends on the rate at which material transfers to the drop surface and the rate at which the material is incorporated into the drop. For vapors, Brownian diffusion is the dominant transfer mechanism by which molecules of the material move to the vapor surface. At the drop surface the molecules must be taken into solution to be removed from the gas, which is why it is important to use liquids in which the vapor to be removed is soluble. The dissolved vapor will produce a partial pressure at the drop surface that will retard further mass transfer to the drop surface. As the vapor pressure of the vapor in the gas decreases, it is possible for the dissolved molecules to leave the drop and re-vaporize back into the gas. For this reason, it is necessary for the molecules to be bound or neutralized within the drop liquid reducing the vapor partial pressure at the drop surface.

For particles, the transfer mechanisms are dominated by Brownian diffusion for small particles (<0.1 micrometer), interception for intermediate sized particles (nominally around 1 micrometer) and impaction for large sized particles (>10 micrometer). Electrostatic effects produced by charged drops will enhance collection rates over the range of particle sizes. When the particle contacts the drop surface, it may be collected or bounce off. If the particle is collected, it is helpful if the decontamination fluid wets the particle so that the particle adheres more strongly to the drop, becomes incorporated into the drop, and is removed (scavenged) from the cloud with the drop.

In addition to physically removing (scavenging, knocking-down) aerosolized toxic materials by spraying a decontamination liquid into the toxic cloud, the decontamination spray should also chemically neutralize and/or deactivate the toxic material while the material is still airborne. Also, the decontamination spray should preferably be non-toxic itself, non-corrosive, and water-based.

The "DF-200" family of aqueous decontamination formulations, which are described in more detail in the related patent applications listed above, meets these requirements for being non-toxic and non-corrosive. DF-200 has been shown to be very effective for neutralizing and decontaminating surfaces contaminated by a wide range of chemical or biological warfare agents (e.g., anthrax spores, *Yersinia pestis*, mustard gas, GD/VX/HD nerve gas agents) and toxic industrial chemicals (e.g., hydrogen cyanide, sodium cyanide, butyl isocyanate, capsaicin, anhydrous ammonia, phosgene, carbon disulfide, malathion).

Against this background, the present invention was developed.

SUMMARY OF THE INVENTION

The present invention relates generally to methods and systems for knockdown and neutralization of toxic clouds of aerosolized chemical or biological warfare (CBW) agents and toxic industrial chemicals using a non-toxic, non-corrosive aqueous decontamination formulation.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Figure 1:
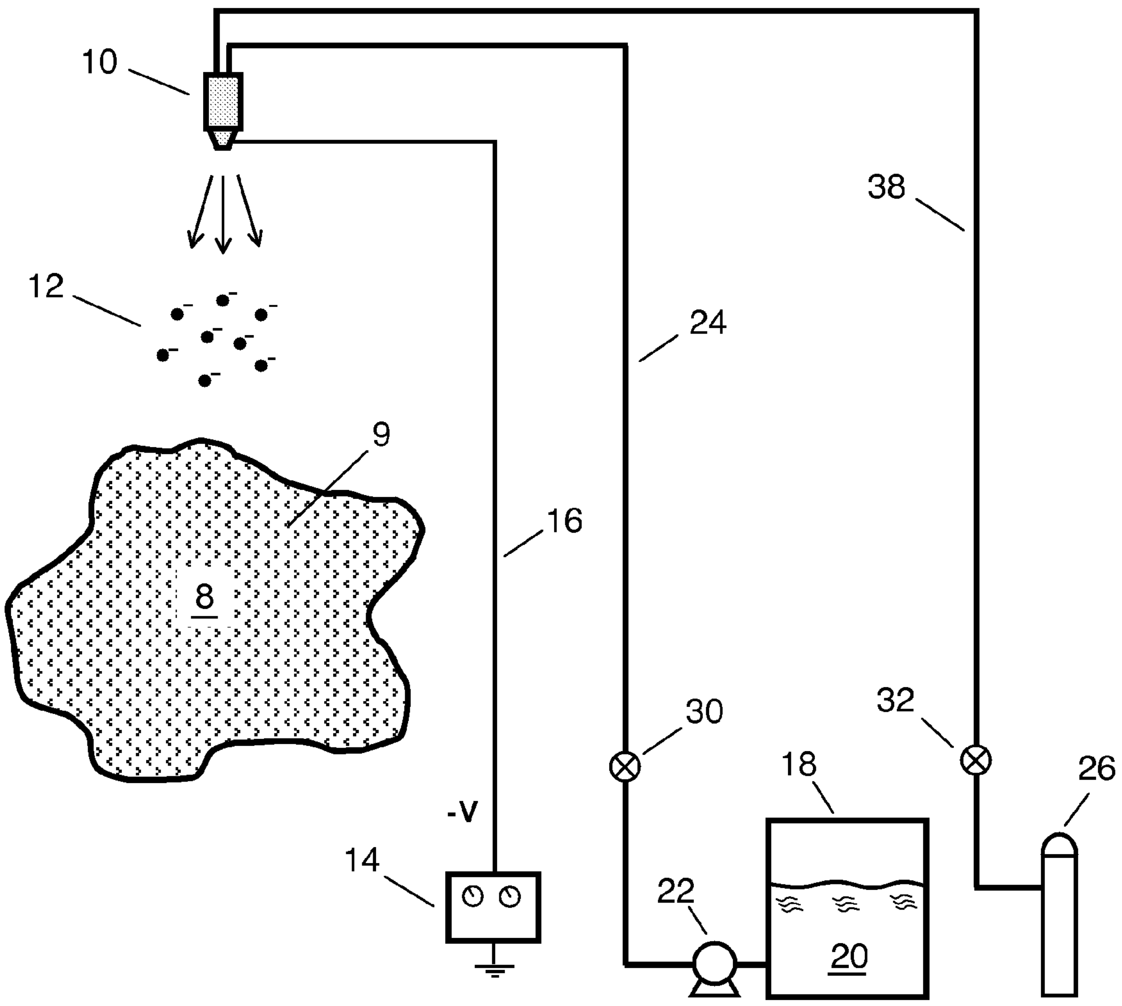
FIG. 1 shows a schematic view of an example of a basic decontamination spray knockdown system, according to the present invention.

Model based analysis was performed in the early stages of development and proof of concept. A spray chamber with diagnostics to measure spray drop size distributions and concentration was available, and was utilized to perform model development, validation, and calibration. A Gaussian plume model of the toxic cloud was used to estimate the challenge presented to our conceptual mitigation methods. The plume modeling results indicate that protection of a specified area in the plume path may be achieved using a spray dispersion system upwind of the area to be protected. The scheme entails use of a sprayed neutralizer solution (i.e., DF-200) dispersed from a fixed location into the path of the contaminant laden plume so that the plume motion itself would produce the means to mix the neutralizing spray drops into the plume so that facilities and people downwind of the dispersion location would be exposed to a neutralized plume. Based on preliminary modeling, negatively-charged DF-200 spray concentrations on the order of 10 to 200 $g/m^3$ were expected to be effective. This was based on a 50:1 challenge ratio (i.e., the ratio of decontaminant solution concentration to toxic agent concentration), and would likely be met. However, a limiting step may be the drop-agent interaction rate, as was reflected in the chamber results. Alternatively, the challenge ratio can be as low as 40:1, based on the most favorable G-simulant tests.

In one embodiment of the present invention, the concentration of DF-200 sprayed into the toxic cloud can be about 50 to 150 $g/m^3$. Also, the duration of spraying the DF-200 formulation can be about 1 minute. Experimental tests have shown that a spray duration of as short as 1 minute is sufficient to cause an immediate 4-log decrease in concentration of toxic material (simulant). Spray durations of as short as 15 seconds have also been shown to cause a greater than 2-log decrease in G-simulant concentration.

Several different spray deployment schemes can be utilized, in which drops of sprayed neutralizer solution would be mixed into the plume as it passed by. The first is to use large fans to draw upwind air through a spray stream, which would produce a high velocity flow of well-mixed air and drops that would expand downwind. A series of these devices placed perpendicular to the plume travel direction would generate a decontaminated zone downwind of the sprayers that would protect people and facilities. A second scheme uses an array of sprays in a balloon-supported curtain to saturate the plume as it passes through the curtain. This idea would produce the same result. Other possibilities include ground or tower mounted sprays to produce the same effect as a curtain. Finally, ground-based systems, which distribute a dry, encapsulated form of the decontaminant, are another possible option. Other applications of using the DF-200 knockdown decontamination spray system include decontamination of holding tanks, personnel decontamination, and decontamination of surfaces.

FIG. 1 shows a schematic view of an example of a charged decontamination spray knockdown system, according to the present invention. Toxic cloud 8 comprises aerosolized particles, drops, and/or vapors of one or more toxic materials 9, such as chemical or biological warfare agents (anthrax spores, *Yersinia pestis*, mustard gas, GD/VX/HD nerve gas agents, etc.) and/or toxic industrial chemicals (hydrogen cyanide, phosgene, carbon disulfide, malathion, etc.). DF-200 aqueous decontamination fluid 20 is stored in storage tank 18, and pumped by pump 22 through liquid supply line 24 to electrostatic spray nozzle(s) 10, which sprays a fog or mist of negatively charged drops (droplets) 12 of decontamination solution. The small droplets are created by the flow of pressurized air supplied to nozzle 10, supplied from pressure tank 26 via air supply line 38. Power supply 14 provides a source of negative voltage, −V, to nozzle 10, for imparting a net negative charge on the sprayed droplets 12. The charged droplets 12 are sprayed into toxic cloud 8, where they combine and chemically react with the aerosols of toxic material 9, thereby neutralizing them and rendering them harmless. The neutralized aerosols then fall down from the cloud to the ground (i.e., are scavenged, knocked-down). Valves 30 and 32 control the flow of liquid and gas to nozzle 10, respectively.

Typically, DF-200 decontamination formulations are stored as 2, 3, or 4 parts as a "kit" configuration, and then pre-mixed (along with adding water), just prior to use. This is because the made-up DF-200 solution, ready to use, has a limited shelf life (typically, less than 24 hours). Preferably, the made-up solution is used in less than 8 hours. In the experiments described later, the three parts (A, B, & C) of a standard DF-200 3-part kit configuration were pre-mixed with water (to make the solution ready-for-use) approximately 15 minutes before use. In these experiments, the three parts were hand mixed in a 2-gallon jug. However, in a large, automated system, the three individual components (e.g., Parts A, B, and C), can be stored in separate containers, and then fed to a mixing chamber by individual feed pumps, with water being added to the mixing chamber, where all of the ingredients are mixed together to make the made-up DF-200 solution. The made-up solution is then provided to storage tank 18 and pump 22, as before in FIG. 1. In this way, the separate components of DF-200 are pre-mixed before entering the spray nozzles.

Optional equipment can be added to the system of FIG. 1, such as: biological or chemical detectors/sensors to provide real-time feedback of cloud concentrations; and weather gauges (thermometer, anemometer, barometer, humidity sensors, wind direction, etc.) to provide data on environmental conditions. Of course, the number of spray nozzles, size, supply lines, flow rates, etc. can be increased and scaled up as necessary to treat a larger size of toxic cloud(s), as needed. Other optional equipment can include flow meters to measure fluid flow rates, pressure gauges, control panels/systems to control the system of valves and nozzle-charging power supply, data acquisition system, pressure relief valves, in-line filters, etc.

The spray nozzle 10 can be a two-fluid type, air-atomizing induction charging nozzle, operating with an air pressure range of 20-100 psi, preferably about 80-95 psi; with a induction voltage of −500 to −2000 V, preferably about −1600 V. The decontamination fluid can be supplied to the nozzle at a pressure no more than about 150 psi, with a fluid flow rate of 50 to 250 mL/minute (per nozzle), preferably about 220 mL/minute. Nozzle 10 can produce negatively charged micro-droplets (i.e., a fog or mist) that can range in size from 10 to 100 microns, and most typically are from 30 to 40 microns. At higher air pressure, about 90-95 psi, the droplet size can be as small as about 10 microns. In general, a smaller droplet size provides more surface area for decontamination than with larger drops. The electrostatic nozzles can be, for example, manufactured by Electro Static Spraying Systems, Inc. of Watkinsville, Ga. (ESS MaxCharge™ nozzles).

In one embodiment, the DF-200 droplets are sprayed from an electrostatic induction spray nozzle operating with an applied voltage of about 1500 to 2000 Volts; with an air pressure of about 80 to 100 psi, and with a DF-200 liquid flow rate of about 200 to 250 mL/minute (per nozzle), preferably about 220 mL/minute.

Alternatively, the sprayed droplets of DF-200 decontamination solution can be generated by pneumatic or rotary atomizers, or thermal drop generation systems. Alternatively, a co-dispersal of two different drop size distributions may be used, a small one suitably tailored to scavenge the airborne contaminant and a larger one also suitably tailored to hasten the fallout of the smaller distribution. In this case, two different size nozzles can be used side-by-side to generate the co-dispersion of the small and large droplet sizes; or the same nozzles operating at two different air pressures (low pressure for larger drops, and higher pressure for smaller drops).

In some embodiments, the spray nozzles may be mounted on elevated platforms (e.g., balloons, towers, cherry pickers). Or, they may be ground based systems, such as dispersion into large fans (e.g. orchard sprayers). Deployment systems may be either stationary, fixed in place (as needed for accidental release of a known process, such as at a chemical facility) or mobile, with the ability to be relocated, such as required for complete perimeter protection of a military base. Deployment systems may be made of any number of individual units, which may be located at strategically advantageous locations and/or elevations, relative to the toxin threat or relative to the open bounded area of protection. In addition to the knockdown and neutralization spray system, deployment systems may include ancillary hardware such as an anemometer, barometer and detector/sampling system to provide real time feedback of cloud concentration and environmental conditions.

Sandia National Laboratories has developed, demonstrated and commercialized an aqueous-based decontamination technology (DF-200) that is effective for neutralizing chemical and biological warfare agents and many toxic industrial chemicals, has low toxicity and corrosivity properties, can work on a number of anticipated material surfaces, and can be incorporated into a number of carriers (foams, liquid sprays, fogs) that satisfy a wide variety of operational objectives. DF-200 was procured by the US Military and staged in the Middle East as part of Operation Iraqi Freedom; in 2005, DF-200 was procured and staged in Korea. An earlier version of the technology (DF-100) was used to remediate portions of the U.S. Capitol Hill office buildings following the anthrax incidents of October 2001.

As background information, live agent tests of DF-200 on surfaces contaminated with three CW agents (GD, VX, and HD) and the biological agents (*Bacillus anthracis* spores and *Yersinia pestis*) were conducted at independent laboratories. Results for kinetic testing of DF-200 on CW agents in stirred reactors are shown in Table 1 and results of tests against anthrax spores and vegetative bacterial cells of *Yersinia pestis* are shown in Table 2 (minimum contact time tested was 15 minutes). Tests against toxic industrial chemicals such as hydrogen cyanide, phosgene, carbon disulfide, and malathion have also been successful and are shown in Table 3.

TABLE 1

Percent decontamination from kinetic tests against CW agents (U.S. DOD).

| | GD | | VX | | HD | |
|---|---|---|---|---|---|---|
| Decontaminant | 10 Min. | 60 Min. | 10 Min. | 60 Min. | 10 Min. | 60 Min. |
| DS2 | >99.9 | >99.9 | >99.9 | >99.9 | >99.9 | >99.9 |
| DF-200 | >99.9 | >99.9 | >99.9 | >99.9 | 69 | >99.9 |

TABLE 2

Results of DF-200 solution tests against anthrax spores and *Y. pestis* vegetative cells (Illinois Institute of Technology Research Institute).

| | *B. anthracis* - Ames RIID | | *B. anthracis* - ANR-1 | | *Y. pestis* (ATCC 11953) | |
|---|---|---|---|---|---|---|
| Contact Time | Average CFU/ml | Log Reduction | Average CFU/ml | Log Reduction | Average CFU/ml | Log Reduction |
| Control | $1.21 \times 10^7$ | 0 | $6.42 \times 10^7$ | 0 | $1.33 \times 10^7$ | 0 |
| 15 Minutes | No Growth | 7 | No Growth | 7 | No Growth | 7 |
| 30 Minutes | No Growth | 7 | No Growth | 7 | No Growth | 7 |
| 60 Minutes | No Growth | 7 | No Growth | 7 | No Growth | 7 |

TABLE 3

Results of modified DF-200 formulations in neutralization of Toxic Industrial Chemicals

| | Challenge | % Decontaminated in solution/ % Decontaminated in headspace | | |
|---|---|---|---|---|
| TIC | Ratio, Solution:TIC | 1 minute | 15 minutes | 60 minutes |
| Hydrogen Cyanide (gas) | 250:1 | 59 | 83 | >99/>99 |
| Hydrogen Cyanide (gas) | 1:1 | 96 | 95 | 48/96 |
| Sodium Cyanide (solid) | 200:1 | 93 | 98 | >99/>99 |
| Phosgene (gas) | 200:1 | 98 | >99 | >99 |
| Carbon Disulfide (liquid) | 200:1 | >99 | >99 | >99 |
| Malathion (liquid) | 200:1 | 89 | 95 | Below detection |
| Capsaicin (liquid) | 200:1 | >99 | Below detection | Below detection |

During 2001 and 2002, Sandia National Laboratories was funded under the DARPA Immune Building program to develop a knockdown spray system that utilized a modified version of the Sandia formulation to rapidly knockdown and decontaminate CBW agents in the event of a release inside of a building. As part of this effort Sandia designed, constructed, and installed a full-scale prototype in the Battelle ISE tested. Testing completed at Sandia's Aerosol Test facility in 2001 and 2002 demonstrated significant knockdown of particles and vapors. Knockdown and decontamination of greater than an order of magnitude of chemical agent simulants was achieved. Using a 1-minute spray of DF-200K, knockdown and decontamination of weaponized *Bacillus globigii* spores was demonstrated achieving 3+ orders of magnitude reduction in spore concentration within 6 minutes and greater than 8 orders of magnitude reduction in spore concentration within ~45 minutes. A total of approximately 4.5 gallons (17.0 liters) of DF-200K was deployed over the 1-minute spray duration through standard spray nozzles. This was a challenge ratio of about 800:1.

The word "formulation" is defined herein as the activated product or solution (e.g., aqueous solution) that is applied to a surface or body for the purpose of neutralization, with or without the addition of a gas (e.g., air) to create foam. Unless otherwise specifically stated, the concentrations, constituents, or components listed herein are relative to the weight percentage of the overall activated solution. The word "water" is defined herein to broadly include: pure water, tap water, deionized water, demineralized water, saltwater, or any other liquid consisting primarily of $H_2O$.

One example of a minimum set of constituents for a DF-200 formulation that can achieve a significant rate of spore kill comprises four components:

(1) a solubilizing agent selected from the group consisting of a cationic surfactant (e.g., Variquat 80MC), a cationic hydrotrope (e.g., Adogen 477), and a fatty alcohol (e.g., 1-Dodeconal);

(2) a beaching activator selected from the group consisting of O-acetyl, N-acetyl, and nitrile group peroxide activators (e.g., propylene glycol diacetate);

(3) a reactive compound (e.g., hydrogen peroxide, peracetic acid); and (4) water.

The solubilizing agent serves to effectively render the toxant susceptible to attack, while the reactive compound serves to attack and neutralize the toxant, and the bleaching activator enhances the process.

Examples of suitable cationic surfactants include: quaternary ammonium salts and polymeric quaternary salts. Examples of suitable quaternary ammonium salts include: cetyltrimethyl ammonium bromide, benzalkonium chloride, benzethonium chloride, cetylpyridinium chloride, alkyldimethylbenzylammonium salt, and tetrabutyl ammonium bromide. A preferred cationic surfactant is VARIQUAT 80MC™ (which used to be supplied by WITCO, Inc., but now is supplied by Degussa Goldschmidt), which is a mixture of benzyl (C12-C16) alkyldimethylammonium chlorides. The concentration of quaternary ammonium salt used in DF-200 formulations is preferably no more than about 10%, because at higher concentrations the quaternary ammonium salt becomes significantly toxic to humans and the environment.

Examples of suitable cationic hydrotropes include: tetrapentyl ammonium bromide, triacetyl methyl ammonium bromide, and tetrabutyl ammonium bromide. A preferred cationic hydrotrope is ADOGEN 477™ (which used to be supplied by WITCO, Inc., but now is supplied by Degussa Goldschmidt), which is a pentamethyltallow alkyltrimethylenediammonium dichloride.

Examples of suitable fatty alcohols include alcohols having 8-20 carbon atoms per molecule, such as: 1-dodecanol, pure dodecanol, hexadecanol, and 1-tetradecanol.

Examples of suitable reactive compounds include: peroxide compounds; hydrogen peroxide; urea hydrogen peroxide; sodium perborate; sodium percarbonate; sodium carbonate perhydrate; sodium peroxypyrophosphate; sodium peroxysilicatehydrogen; peroxide adducts of pyrophosphates; citrates; sodium sulfate; urea; and sodium silicate; an activated peroxide compound (e.g., hydrogen peroxide+bicarbonate); peracetic acid; oximates (e.g., butane-2,3-dione, monooximate ion, and benzohydroxamate); alkoxides (e.g., methoxide and ethoxide); aryloxides (e.g., aryl substituted benzenesulfonates); aldehydes (e.g., glutaraldehyde); peroxymonosulfate; Fenton's reagent (a mixture of iron and peroxide); and sodium hypochlorite. Use of these reactive compounds in DF-200 formulations can produce a variety of negatively-charged nucleophiles, e.g., hydroxyl ions ($OH^-$) and hydroperoxide ions (($OOH^-$) produced when using hydrogen peroxide; and/or hydroperoxycarbonate ions ($HCO_4^-$) produced when hydrogen peroxide is combined with a carbonate salt. Hydroperoxycarbonate ions ($HCO_4^-$) are a much stronger oxidant than hydroxyl ions ($OH^-$) or hydroperoxide ions (($OOH^-$), and are especially effective in reacting with biological toxants. When using hydrogen peroxide in DF-200 formulations, its concentration is preferably less than about 10% because higher concentrations are significantly corrosive, especially in the range of 30-50% hydrogen peroxide concentration.

To achieve very high rates of spore kill, a carbonate salt (e.g., sodium bicarbonate or potassium bicarbonate) is preferably added to the minimum set of constituents for DF-200 formulations described above. When using a peroxide compound (e.g., hydrogen peroxide) as the reactive compound for DF-200, the added carbonate salt combines with, e.g., hydrogen peroxide to form the highly reactive hydroperoxycarbonate species ($HCO_4^-$). Addition of carbonate salts can also buffer the formulation to optimize the pH.

Hence, a minimum set of constituents for DF-200 formulations that can achieve a very high rate of spore kill can comprise five components:

(1) a solubilizing agent selected from the group consisting of a cationic surfactant (e.g., Variquat 80MC), a cationic hydrotrope (e.g., Adogen 477), and a fatty alcohol (e.g., 1-Dodeconal);

(2) a beaching activator selected from the group consisting of O-acetyl, N-acetyl, and nitrile group peroxide activators (e.g., propylene glycol diacetate);

(3) a reactive component (e.g., hydrogen peroxide, peracetic acid, etc.);

(4) a carbonate salt (e.g., sodium bicarbonate); and (5) water.

Examples of suitable carbonate salts include: potassium bicarbonate, sodium bicarbonate, ammonium bicarbonate, ammonium hydrogen bicarbonate, lithium bicarbonate, ammonium carbonate, and potassium carbonate.

Next, a variety of alternative embodiments and configurations of DF-200 formulations will be presented.

DF-200HF (High Foam)

An example of a "high-foaming" formulation for DF-200HF comprises:

DF-200HF (High Foam)

1-4%(preferably 2%) Variquat 80MC (cationic surfactant)

0.5-3% (preferably 1%) Adogen 477 (cationic hydrotrope)

0.2-0.8% (preferably 0.4%) 1-Dodecanol (fatty alcohol)

0.05-0.1% Jaguar 8000 (cationic water-soluble polymer)

0.5% Di(propylene glycol) Methyl Ether (solvent)

0.1-10% (preferably 1-4%) Hydrogen Peroxide (oxidant)

0.1-10% (preferably 2-8%) Bicarbonate salt (buffer and peroxide activator)

1-4% Propylene Glycol Diacetate or Glycerol Diacetate (bleaching activator)

67-97% Water

This formulation is effective at a pH value between 7.5 and 10.5. This formulation can be adjusted to a pH value between 9.6 and 9.8 for optimal decontamination of all target agents.

This "high-foam" formulation includes a cationic water-soluble polymer (e.g., Jaguar 8000™ or), which increases the bulk viscosity of the solution and produces a more stable foam. Some examples of other suitable non-anionic water-soluble polymers include: polyvinyl alcohol, guar gum, (cationic or non-ionic) polydiallyl dimethyl ammonium chloride, polyacrylamide, polyethylene glycol 8000 (e.g., PEG 8000), and Jaguar 8000™ (Guar Gum 2-hydroxypropyl ether). A cationic polymer is preferred over a non-ionic polymer; an anionic polymer does not work well. The fatty alcohol 1-dodecanol serves to increase the surface viscosity of the foam lamellae to also increase foam stability against drainage and bubble collapse. Other foaming agents may also be included in the high-foaming formulations, namely Celquat SD 240c (at about 0.15%) and/or Lumulse POE 12 (at about 4%).

DF-200LF (Low Foam)

An example of a "low-foaming" formulation for DF-200LF comprises:

DF-200LF (Low Foam)

4% Variquat 80MC (cationic surfactant)

0.4% Lauramide DEA [N,N-Bis(2-Hydroxyethyl)-Dodecanamide] (foam booster)

1-4% Propylene Glycol Diacetate or Glycerol Diacetate (bleaching activator)

0.5% Di(propylene glycol) Methyl Ether (solvent)

0.05-0.1% Jaguar 8000 Polymer (cationic water-soluble polymer)

0.1-10% (preferably 1-4%) Hydrogen Peroxide (oxidant)

0.1-10% (preferably 2-8%) Bicarbonate salt (buffer and peroxide activator)

71-94% Water

This formulation is generally effective at a pH value between 7.5 and 10.5. This formulation can be adjusted to a pH value between about 9.6 and 9.8 for optimal decontamination of all target agents.

The term 'High Foam' refers to the ability of a formulation to form a highly stable and persistent foam, whereas a 'Low Foam' formulation forms a much less stable foam. The following tables show the improved performance of DF-200HF and DF-200LF as compared to DF-100A. The notation "ND" refers to a concentration below detectable limits, and "PGDA" refers to propylene glycol diacetate (a preferred bleaching activator).

TABLE 4

Summary of the reaction rates for Mustard simulant (2-Chloroethyl phenyl sulfide).

| Formulation | Mustard Simulant (% Decontaminated) 1 Minute | 15 Minutes | 60 Minutes |
|---|---|---|---|
| DF-100A (pH 8) | 18 | 42 | 81 |
| DF-100A (pH 9.2) | 16 | 38 | 83 |
| DF-200HF (2% PGDA/3% $H_2O_2$/4.5% Bicarb) | 42 | 62 | ND |
| DF-200HF (2% PGDA/3.5% $H_2O_2$/4% Bicarb) | 94 | 98 | ND |
| DF-200LF (2.5% PGDA/3% $H_2O_2$, 4.5% Bicarb) | 55 | 91 | ND |

TABLE 5

Summary of the reaction rates for VX simulant (0-Ethyl S-Ethyl Phenylphosphonothioate).

| Formulation | VX Simulant (% Decontaminated) 1 Minute | 15 Minutes | 60 Minutes |
|---|---|---|---|
| DF-100A (pH 10) | 45 | 99 | ND |
| DF-100A (pH 9.2) | 33 | 71 | 93 |
| DF-200HF (2% PGDA/3% $H_2O_2$/4.5% Bicarb) | 63 | 98 | ND |
| DF-200HF (2% PGDA/3.5% $H_2O_2$/4% Bicarb) | 66 | 99 | ND |
| DF-200LF (2.5% PGDA/3% $H_2O_2$/4.5 Bicarb) | 79 | 98 | ND |

TABLE 6

Summary of the reaction rates for G Agent simulant (Diphenyl chlorophosphate).

| Formulated | G Agent Simulant (% Decontaminated) 1 Minute | 15 Minutes | 60 Minutes |
|---|---|---|---|
| DF-100A (pH 8) | 53 | ND | ND |
| DF-100A (pH 9.2) | ND | ND | ND |
| DF-200 HF (2% PGDA/3% $H_2O_2$ /4.5 Bicarb) | ND | ND | ND |
| DF-200HF (2% PGDA/3.5% $H_2O_2$ 4% Bicarb) | ND | ND | ND |
| DF-200LF (2.5% PGDA/3% $H_2O_2$ 4.5% Bicarb) | ND | ND | ND |

TABLE 7

Summary of the kill rates for Anthrax simulant (*Bacillus globigii* spores)

| Formulation | Anthrax Simulant % Kill after 30 Minutes | Anthrax Simulant % Kill after 60 Minutes |
|---|---|---|
| DF-100A (pH 8) | 99.99 | 99.99999 |
| DF-100A (pH 9.2) | 90 | 99.9 |
| DF-200HF (2% PGDA/3% $H_2O_2$/ 4.5 Bicarb) | 99.99999 | 99.99999 |
| DF-200LF (2.5% PGDA/3% $H_2O_2$/ 4.5 Bicarb) | 99.99999 | 99.99999 |

DF-200 formulations are active against all agents at a single pH. The formulation is effective at pH values between about 7.5 and 10.5; is more effective at pH values between about 9.2 and 9.8; and is most effective at pH values between about pH 9.6 and 9.8.

DF-200 formulations include a bleach/bleaching activator, which can be a compound with O— or N— bounded acetyl groups that react with the strongly nucleophilic hydroperoxy anion ($OOH^-$) to yield peroxygenated species that are more efficient oxidizers than hydrogen peroxide alone.

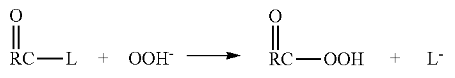

Since the 1950's, a number of different bleaching activators have been used in commercial laundry detergents, as well as other commercial products. The most common activators are tetraacetyl ethylenediamine (TAED), which is primarily used in Europe and Asia; and n-nonanoyloxybenzenesulfonate (NOBS), which is primarily used in the United States. NOBS is a proprietary chemical of the Proctor and Gamble company. In a laundry detergent, hydrogen peroxide is provided in a solid form (usually as sodium perborate, which reacts in water to form the hydroperoxy anion). The addition of a bleaching activator greatly enhances the ability of a laundry detergent to remove stains from clothing.

It should be noted that TAED and NOBS bleaching activators are extremely insoluble in water (e.g., TAED is only 0.1% soluble at 25° C.). To get around this problem in a laundry detergent, the solid TAED or NOBS particles are kept in suspension by the agitating action of the washing machine, where they slowly react with the hydrogen peroxide in the detergent. However, agitation in the field of DF-200 formulations presents practical problems; hence, a water-soluble bleaching activator is preferred. Clogging of spray nozzles is also a concern with insoluble particles.

Examples of suitable water-soluble bleaching activators include short-chained organic compounds that contain an ester bond, e.g., ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, and propylene glycol diacetate. A preferred water-soluble bleaching activator is propylene glycol diacetate (PGDA), which is shown below.

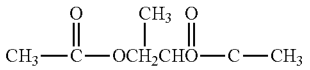

This molecule reacts with hydroperoxy anions ($OOH^-$), giving up the ester bonds to form two peroxygenated molecules.

Propylene glycol diacetate also acts as an organic solvent that is highly effective in solubilizing insoluble organic molecules (e.g., chemical warfare agents, as well as foam stabilizers/boosters (such as 1-dodecanol and Lauramide DEA)). Therefore, an added function of this compound is that it can be used to supplement the diethylene glycol monobutyl ether (DEGMBE) solvent that is used in DF-100 and DF-100A, or to supplement the Di(propylene glycol) methyl ether or propylene glycol solvent used in some DF-200 formulations, thereby allowing the propylene glycol diacetate to serve a dual purpose (i.e., solvent and bleaching activator).

Bleaching activators are generally not stable in water for long periods of time. This is especially true when the aqueous solution is at a high pH (>10). Therefore, for long shelf life, the propylene glycol diacetate (or other bleaching activator) is preferably stored separate from the aqueous solution until use. This is not unlike other products that utilize bleach activators (e.g., laundry detergents), where all the components of the formulation are kept dry and separated until use (in the case of laundry detergent, the bleaching activator is encapsulated to prevent it from reacting with the peroxide component until both components are mixed in water).

Another example of a water-soluble bleaching activator is ethylene glycol diacetate, which works well in DF-200 formulations. However, when ethylene glycol diacetate reacts with hydrogen peroxide, it forms ethylene glycol (i.e., antifreeze), which is a relatively toxic byproduct. Propylene glycol diacetate, on the other hand, does not form this relatively toxic byproduct.

DF-200NF (Non-Foaming)

An example of a non-foaming DF-200 formulation comprises (amounts illustrative):

DF-200NF (Non-Foaming)

1-10% (preferably 2.5%) Benzalkonium Chloride (cationic surfactant)

1-8% Propylene Glycol Diacetate or Glycerol Diacetate (bleaching activator)

1-16% Hydrogen Peroxide (oxidant)

2-8% Potassium Bicarbonate (buffer and peroxide activator)

65.5-93.5% Water

The formulation can be adjusted to a pH value between about 9.6 and 9.8 for optimum performance, and is effective for decontamination of all target agents.

Other bleaching activators (such as water-insoluble NOBS or TAED) can be used in place of Propylene Glycol Diacetate in DF-100E. However, as noted above, this produces a slurry mixture instead of a true liquid solution.

In general, activated DF-200 formulations are used preferably within 8 hours after mixing, however, they still can be effective for up to 24 hours and longer. DF-200HF (High Foam) can be applied to a surface for a long period of time, and then rinsed off. However, DF-200LF (Low Foam) can be used in a different manner than the DF-100/100A and DF-200HF formulations. Instead of leaving DF-200LF on a surface for long periods of time, it can be applied to a surface, left for a relatively short period of time (e.g., 15-60 minutes), and then rinsed off with a high-pressure freshwater or saltwater spray. This will minimize corrosion of the material to which it is applied, which will make it especially useful for decontaminating aircraft and other equipment where corrosion is a concern. It will also minimize the time required for decontamination, which is especially advantageous for military use (on the battlefield or at fixed sites). Saltwater can also be effectively used as the make-up water for DF-200 formulations.

DF-200 Rapid Deployment Configurations

Other embodiments emphasize the rapid deployment of DF-200 formulations, and/or its deployment using small-scale deployment equipment (such as hand-held units, backpack units, or units mounted on small dollies). For these applications, all of the water is 'pre-packaged' into the formulation, so that no extra water is required in the field. A first example of a 3-part kit configuration for a Rapid Deployment version of DF-200HF, "DF-200HF Rapid Deployment #1", comprises (amounts illustrative):

DF-200HF Rapid Deployment #1 (3-Part Kit)

Part A (Liquid Foam Component):
20 g Variquat 80MC
10 g Adogen 477
4 g 1-Dodecanol
5 g Poly(Ethylene Oxide)
8 g Diethylene Glycol Monobutyl Ether
5 g Isobutanol
45 g Potassium Bicarbonate
approx. 19 g Potassium Hydroxide (the pH of Part A should be approximately 10.2)
933 g Water Part B (Solid Oxidant Component):
97 g Urea Hydrogen Peroxide Part C (Liquid Bleaching Activator):
20 g Propylene Glycol Diacetate or Glycerol Diacetate This configuration will produce 1 liter of foam solution. The pH of the final formulation can be adjusted to be between about 9.6 and 9.8 for optimal performance. The following mixing procedure can be used: Mix Part B into Part A. After dissolution of the urea hydrogen peroxide, add Part C to Part A+B. Use, preferably, within 8 hours. The performance of DF-200HF Rapid Deployment against chemical agent simulants is shown below in Table 8:

TABLE 8

Reaction rates from kinetic testing of DF-200HF Rapid Deployment #1 configuration.

| | % Decontaminated | | |
|---|---|---|---|
| Simulant | 1 Minute | 15 Minutes | 60 Minutes |
| Mustard (HD) | 48 | 82 | ND |
| G Agents | ND | ND | ND |
| VX | 71 | 97 | >99 |

Tests against the anthrax spore simulant (*Bacillus globigii* spores) demonstrated 99.9999% (7-Log) kill after a 30-minute exposure to DF-200HF Rapid Deployment.

Urea hydrogen peroxide dissolves rapidly in water. Therefore, the formulation can be prepared and deployed in a very short time at the scene of an incident involving chemical or biological warfare agents, making it ideal for use by civilian first responders (firefighters, HazMat units, police officers, and others who would be the first to arrive at the location of a CBW attack), and/or the military.

However, the particular bleaching activator (propylene glycol diacetate) used in this formulation is not stable in an aqueous solution where the pH is greater than approximately 9.9. Therefore, it is important to mix the right components in the correct order. For example, if Part C is mixed into Part A before the addition of Part B, there may be some loss of activity in DF-200HF since the propylene glycol diacetate is exposed to a solution having a pH value >9.9. This is not true, however, if Part B is added to Part A before the addition of Part C, since the addition of Part B to Part A brings the pH of the Part A+B mixture to a value below about 9.9.

The solvent, diethylene glycol monobutyl ether, used in Part A (the foam solution) of the first example shown above for DF-200HF Rapid Deployment #1 is different than the solvent that was used in the previously described DF-200HF formulation (Di(propylene glycol) methyl ether), because Di(propylene glycol) methyl ether is not stable in the high pH environment required for the foam component (Part A) in the rapid deployment configuration. Also, note that a short-chained alcohol (i.e., isobutanol) has been added to the foam component (Part A) in the rapid deployment configuration #1 of DF-200HF. While this low molecular weight alcohol can cause flammability problems in highly concentrated configurations of DF-200HF, it is not a problem in the less concentrated configurations described herein. The use of isobutanol also helps solubilize the 1-dodecanol in Part A, and improves the kinetics (chemical reactivity) of the formulation. In addition, the formulation preferably uses a different polymer, poly(ethylene oxide), than the polymer used in the other earlier described DF-200 formulations (i.e., Jaguar 8000). This alternative polymer is used because Jaguar 8000 is also not stable in the high pH environment of the liquid foam portion (Part A) of the rapid deployment formulation. Accordingly, a preferred formulation for DF-200HF Rapid Deployment #1 comprises:

DF-200HF Rapid Deployment #1

1-4% (preferably 2%) Variquat 80MC (cationic surfactant)

0.5-3% (preferably 1%) Adogen 477 (cationic hydrotrope)

0.2-0.8% (preferably 0.4%) 1-Dodecanol (fatty alcohol)

0.5-8% (preferably 0.5%) Poly(Ethylene Glycol) (polymer)

0.6-1.2% (preferably 0.8%) Diethylene Glycol Monobutyl Ether (solvent)

0-1% (preferably 0.5%) Isobutanol (short-chained alcohol)

0.1-10% (preferably 2-8%) Bicarbonate salt (buffer and peroxide activator)

0.1-10% (preferably 1-4%) Hydrogen Peroxide (oxidant)

0.1-10% (preferably 1-4%) Propylene Glycol Diacetate (bleaching activator)

52-97% Water

The formulation can be adjusted to a pH value between about 9.6 and 9.8 for optimal performance, and is effective for decontamination of all target agents.

A second example of a 3-part kit configuration for a Rapid Deployment version of DF-200HF, "DF-200HF Rapid Deployment #2", comprises (amounts illustrative):

DF-200HF Rapid Deployment #2 (3-Part Kit)

Part A (Liquid Foam Component):

20 g Variquat 80MC 10 g Adogen 477

4 g 1-Dodecanol 20 g Polyethylene Glycol 8000 polymer 8 g Diethylene Glycol Monobutyl Ether 5 g Isobutanol 50 g Potassium Bicarbonate approx. 25 g Potassium Hydroxide (the pH of Part A should be about 10.2)

933 g Water

Part B (Solid Oxidant Component):

97 g Urea Hydrogen Peroxide

Part C (Liquid Bleaching Activator):

20 g Propylene Glycol Diacetate or Glycerol Diacetate

In this second example, Polyethylene Glycol 8000 polymer replaced the poly (Ethylene Oxide) polymer used in DF-200HF Rapid Deployment #1.

A third example of a 3-part kit configuration for a Rapid Deployment version of DF-200HF, "DF-200HF Rapid Deployment #3", comprises (amounts illustrative):

DF-200HF Rapid Deployment #3 (3-Part Kit)

Part A (Liquid Foam Component):

20 g Variquat 80MC 10 g Adogen 477

4 g 1-Dodecanol 20 g Polyethylene Glycol 8000 polymer 10 g Hexylene Glycol 45 g Potassium Carbonate 5 g Potassium Bicarbonate 700 g Water Part B (Solid Oxidant Component):

83 g Urea Hydrogen Peroxide

Part C (Liquid Bleaching Activator):

20 g Glycol Diacetate (i.e., Diacetin)

In this third example, Polyethylene Glycol 8000 polymer replaced the poly(Ethylene Oxide) polymer used in DF-200HF Rapid Deployment #1 as a water-soluble polymer. Also, Hexylene Glycol replaced Diethylene Glycol Monobutyl Ether and Isobutanol used as a solvents. Finally, Glycol Diacetate (i.e., Diacetin) replaced Propylene Glycol Diacetate used as the bleaching activator. These changes in the third example were made to reduce or eliminate the use of short-chained alcohols and/or high vapor-pressure solvents to prevent possible problems with very long-term (months to years) shelf life of the liquid foam component (Part A), especially at high ambient storage temperatures, due to evaporation of the most-volatile components. Note that the combination of 45 grams of potassium carbonate and the 5 grams of potassium bicarbonate were chosen to supply both the right amount of carbonate/bicarbonate, and to adjust the pH appropriately. Alternatively, 50 grams of potassium bicarbonate could have been used (with no potassium carbonate), and then the right amount of potassium hydroxide (base) could have been added to increase the pH to the desired value, as is well known in the art.

Alternative DF-200 Formulations

Other embodiments of DF-200 formulations are:

1. An alternative formulation that includes propylene glycol to lower the freezing point of the solution;

2. An alternative formulation that utilizes sodium percarbonate as a solid source of hydrogen peroxide;

3. An alternative formulation that includes a corrosion inhibitor;

4. An alternative formulation that includes glycerol as a viscosity builder for operations such as skin decontamination;

5. An alternative formulation that utilizes O-acetyl bleaching activators, including one which is available in solid form; and 6. An alternative formulation that utilizes a bleaching activator containing a nitrile group.

DF-200 with Propylene Glycol

The following is a first example of a 2-part kit configuration for DF-200HF that includes propylene glycol as a freezing point depressant, and where all of the water is 'pre-packaged' in Part A, comprising (amounts illustrative):

DF-200HF Rapid Deployment with Propylene Glycol, First Example (2-Part Kit)

Part A (Liquid Foam Component):
20 g Variquat 80MC
10 g Adogen 477
20 g Poly(Ethylene Glycol) (MW 8000)
8 g Diethylene Glycol Monobutyl Ether
5 g Isobutanol
4 g 1-Dodecanol
20 g Propylene Glycol Diacetate or Glycerol Diacetate
150 g Propylene Glycol (freeze-point depressant)
approx. 6 g of 10% HCl Solution (sufficient to give a final pH of 2.5 in Part A)
777 g Water Part B (Solid Additive):
97 g Urea Hydrogen Peroxide
12 g Potassium Bicarbonate
38 g Potassium Carbonate (buffer, to adjust final pH)

This formulation will produce 1 liter of foam solution. The pH of the final formulation can be adjusted to be between about 9.6 and 9.8 for optimal performance. A person of ordinary skill in the art will understand that the ratio of potassium carbonate to potassium bicarbonate used in Part B can be adjusted to achieve the desired final pH of the formulation (preferably about 9.6 to about 9.8). Hence, in this example, the potassium carbonate serves as both a base and a source of carbonate/bicarbonate. To prepare this formulation, mix Part B into Part A. Use, preferably, within 8 hours. The performance of this first example of DF-200HF with propylene glycol against chemical agent simulants is shown in Table 9.

TABLE 9

Reaction rates from kinetic testing for DF-200HF with propylene glycol (first example).

| | % Decontaminated | | |
|---|---|---|---|
| Simulant | 1 Minute | 15 Minutes | 60 Minutes |
| Mustard (HD) | 16 | 80 | ND |
| G Agents | ND | ND | ND |
| VX | 66 | 90 | >99 |

Tests against the anthrax spore simulant (*Bacillus globigii* spores) demonstrated 99.9999% (7-Log) kill after a 30-minute exposure to DF-200HF with propylene glycol (first example).

When all of the water is "pre-packaged" in Part A, the mixing of the formulation for use can be accomplished in a very short time since it only consists of two parts. Therefore, it could be deployed very rapidly at the scene of an incident involving chemical and biological warfare agents. This configuration is ideal for use the civilian first responder (firefighter, HazMat units, police officers, and others who would be the first to arrive at the location of a CBW attack). However, it is heavier to carry than other configurations that add water in the field.

This configuration also incorporates the bleaching activator, propylene glycol diacetate, into the foam component Part A (rather than storing it as a separate, third component). This is possible because the pH of the foam component is less than 3. Propylene glycol diacetate will hydrolyze in solutions of pH greater than 3, but is hydrolytically stable in solutions of pH less than 3. This configuration also uses the polyethylene glycol polymer (PEG 8000) for viscosity enhancement. This polymer is used in many cosmetics and is extremely soluble and stable in water. In addition, it is easier to mix into solution than Jaguar 8000 or a high molecular weight poly(ethylene oxide), since it does not have the tendency to clump.

This configuration includes propylene glycol as a freeze-point depressant. Propylene glycol is considered to be an environmentally friendly antifreeze. In this case, the concentration is approximately 15% by weight, which lowers the freezing point of Part A to approximately −20° C. This configuration has also been tested with good results with propylene glycol concentrations as high as 40% by weight.

An alternative to the first example of DF-200HF with Propylene Glycol shown above is to use sodium percarbonate as the source of the bicarbonate and as a portion of the peroxide in Part B, instead of using urea hydrogen peroxide. This substitution is useful because sodium percarbonate is much less expensive than urea hydrogen peroxide. This second example of DF-200HF with Propylene Glycol is shown below (amounts illustrative):

DF-200HF Rapid Deployment with Propylene Glycol, Second Example (2-Part Kit)

Part A (Liquid Foam Component):
20 g Variquat 80MC
10 g Adogen 477
20 g Poly(Ethylene Glycol) (MW 8000)
8 g Diethylene Glycol Monobutyl Ether
5 g Isobutanol
4 g 1-Dodecanol
20 g Propylene Glycol Diacetate or Glycerol Diacetate
150 g Propylene Glycol (freeze-point depressant)
approx. 6 g of 10% HCl Solution (sufficient to give a final pH of 2.5 in Part A)
777 g Water Part B (Solid Additive):
90 g Sodium Percarbonate
15 g Citric Acid (buffer, to adjust final pH)

This formulation will produce 1 liter of foam solution. The pH of the final formulation can be adjusted to be between about 9.6 and 9.8 for optimal performance. The following mixing procedure can be used: Mix Part B into Part A. Use, preferably, within 8 hours.

Alternatively, sodium bisulfate (a common pool conditioning chemical), or other acid, can be used in place of citric acid to adjust the pH. The performance of this second example of DF-200HF with Propylene Glycol (utilizing sodium percarbonate) against chemical agent simulants is shown in Table 10.

TABLE 10

Reaction rates from kinetic testing for the second example of DF-200HF with propylene glycol (utilizing sodium percarbonate).

| | % Decontaminated | | |
|---|---|---|---|
| Simulant | 1 Minute | 15 Minutes | 60 Minutes |
| Mustard (HD) | 80 | ND | ND |
| VX | 76 | 96 | >99 |

In general, sodium percarbonate dissolves much more slowly than urea hydrogen peroxide after it has been added to Part A. However, to increase the dissolution velocity, sodium percarbonate can be milled to approximately a 100-mesh size for use in this configuration. The time to dissolve the sodium percarbonate was decreased from approximately 30 minutes to about 2 minutes when milled sodium percarbonate was used.

DF-200 with Corrosion Inhibitor

Corrosion inhibitors can be added to DF-200 formulations to reduce their corrosivity. A preferred corrosion inhibitor for use in DF-200 formulations is N,N-dimethyl ethanolamine. However, other corrosion inhibitors, such as triethanolamine, ethanolamine salts of C9, C10, and C12 diacid mixtures, dicyclohexyl amine nitrite, and N,N-dibenzylamine, can be used. The Corrosion inhibitors added to DF-200 formulations can serve multiple purposes:

1. a corrosion inhibitor, 2. a pH buffer, 3. a solvent to keep 1-dodecanol in solution, and 4. a co-solvent to solubilize insoluble chemical agents, such as sarin or mustard.

An example of a 3-part kit configuration of DF-200HF with a corrosion inhibitor comprises (amounts illustrative):

DF-200HF Rapid Deployment with Corrosion Inhibitor (3-Part Kit)

Part A (Liquid Foam Component):

20 g Variquat 80MC 10 g Adogen 477

4 g 1-Dodecanol 5 g Poly(Ethylene Glycol)

10 g N,N-dimethyl ethanolamine (corrosion inhibitor)

50 g Potassium Bicarbonate approx. 18 g Potassium Hydroxide (suff. to give a final pH of 10.2 in Part A)

936 g Water

Part B (Solid Oxidant Component):

97 g Urea Hydrogen Peroxide

Part C (Liquid Bleaching Activator):

20 g Propylene Glycol Diacetate or Glycerol Diacetate

This formulation will produce 1 liter of foam solution. The pH of the final formulation can be adjusted to be between about 9.6 and 9.8 for optimal performance. The following mixing procedure can be used: Mix Part B into Part A. Then, after dissolution of the urea hydrogen peroxide, add Part C to Part A+B. Use, preferably, within 8 hours. The performance of DF-200HF with corrosion inhibitor is shown below against chemical agent simulants is given in Table 11.

TABLE 11

Reaction rates in kinetic testing for DF-200HF with a corrosion inhibitor.

| | % Decontaminated | | |
|---|---|---|---|
| Simulant | 1 Minute | 15 Minutes | 60 Minutes |
| Mustard (HD) | 7 | 41 | 79 |
| VX | 58 | 94 | 99 |

Tests against the anthrax spore simulant (*Bacillus globigii* spores) demonstrated 99.9999% (7-Log) kill after a 60-minute exposure to DF-200HF with a corrosion inhibitor. The addition of the corrosion inhibitor has a detrimental effect on the performance of DF-200 against chemical agents, but has no measured effect on the performance of DF-200HF against biological agents. Similar results were obtained when an alternative corrosion inhibitor, 1% triethanolamine, was used.

DF-200 with Glycerol

In another embodiment of a DF-200 formulation, glycerol may be employed as a viscosity builder in place of Jaguar 8000, poly(ethylene oxide), or polyethylene glycol. Glycerol is a common ingredient in cosmetics, where it is used a viscosity builder, as well as a solvent, humectant and emollient. Thus, the use of glycerol in DF-200 formulations can serve multiple purposes:

1. Viscosity builder, 2. a humectant (i.e., a substance which moisturizes the skin), 3. a solvent to keep 1-dedecanol in solution, and 4. a co-solvent to solubilize insoluble chemical agents, such as sarin or mustard.

An example of a 3-part kit configuration of DF-200HF with glycerol comprises (amounts illustrative):

DF-200HF Rapid Deployment with Glycerol (3-Part Kit)

Part A (Liquid Foam Component):

20 g Variquat 80MC 10 g Adogen 477

4 g 1-Dodecanol 40 g Glycerol (viscosity builder)

40 g Potassium Bicarbonate about 17 g Potassium Hydroxide (sufficient to give a final pH of 10.2 in Part A)

906 g Water

Part B (Solid Oxidant Component):

97 g Urea Hydrogen Peroxide

Part C (Liquid Bleaching Activator):

20 g Propylene Glycol Diacetate or Glycerol Diacetate

This formulation will produce 1 liter of foam solution. The pH of the final formulation can be adjusted to be between about 9.6 and 9.8 for optimal performance. The following mixing procedure can be used: Mix Part B into Part A. Then after dissolution of the urea hydrogen peroxide, add Part C to Part +/B. Use, preferably, within 8 hours. The performance of DF-200HF with glycerol against chemical agent simulants is given in Table 12.

TABLE 12

| Reaction rates in kinetic testing for DF-200HF with glycerol. | | | |
|---|---|---|---|
| | Decontaminated | | |
| Simulant | 1 Minute | 15 Minutes | 60 Minutes |
| Mustard (HD) | 63 | 96 | ND |
| G Agents | ND | ND | ND |
| VX | 76 | 99 | ND |

Tests against the anthrax spore simulant (*Bacillus globigii* spores) demonstrated 99.9999% (7-Log) kill after a 30-minute exposure to DF-200HF with glycerol.

This formulation can be used for direct application to humans because the glycerol will act as a humectant. This formulation could also be utilized, e.g., as a spray or shower, by removing foaming constituents (such as 1-dodecanol and Adogen 477), and by reducing the concentration of peroxide. However, a drawback to the use of glycerol is that it is solid at a fairly high temperature (below about 10° C.). Therefore, it would preferably be used in controlled temperature conditions (i.e., warm temperature conditions).

Propylene glycol diacetate, a bleaching activator used in many of the previously described DF-200 configurations is not presently available in solid form. However, other bleaching activators are available in solid form.

DF-200 with Acetylcholine Chloride

Solid O-acetyl bleaching activators (e.g., acetylcholine chloride, which is often used in eye drop solutions) can be used in DF-200 formulations in place of (liquid) propylene glycol diacetate. The chemical structure of this O-acetyl bleaching activator is shown below. As can be seen, the molecule contains an O-acetyl group that can activate peroxide, and it is a quaternary compound, which is very compatible with DF-200 formulations. Acetylcholine chloride is also soluble in water and is very hygroscopic.

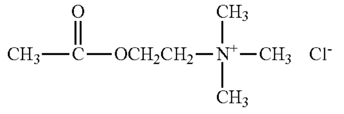

An example of a 2-part kit configuration of DF-200HF using acetylcholine chloride comprises (amounts illustrative):

DF-200HF Rapid Deployment Using Acetylcholine Chloride (2-part kit)

Part A (Liquid Foam Component):

20 g Variquat 80MC
10 g Adogen 477
30 g Poly(Ethylene Glycol) (MW 8000)
8 g Diethylene Glycol Monobutyl Ether
5 g Isobutanol
4 g 1-Dodecanol
150 g Propylene Glycol
50 g Potassium Bicarbonate
approx. 17 g Potassium Hydroxide (suff. to give a final pH of 10.2 in Part A)
803 g Water Part B (Solid Additive):

97 g Urea Hydrogen Peroxide
25 g Acetycholine Chloride (solid bleaching activator)

This formulation will produce approximately 1 liter of foam solution. The pH of the final formulation can be adjusted to be between about 9.6 and 9.8 for optimal performance. To use this formulation, mix Part B into Part A. Use, preferably, within 8 hours. The performance of DF-200HF using acetylcholine chloride against chemical agent simulants is shown in Table 13.

TABLE 13

| Reaction rates from kinetic testing for the DF-200HF using acetylcholine chloride as an activator. | | | |
|---|---|---|---|
| | % Decontaminated | | |
| Simulant | 1 Minute | 15 Minutes | 60 Minutes |
| Mustard (HD) | 60 | 98 | ND |
| VX | 10 | 85 | >99 |

Tests against the anthrax spore simulant (*Bacillus globigii* spores) demonstrated 99.9999% (7-Log) kill after a 30-minute exposure to DF-200HF using acetylcholine chloride.

Two other O-acetyl bleaching activators, monoacetin (glycerol monoacetate) and diacetin (glycerol diacetate), have also been tested for their effectiveness in DF-200 formulations. Both of these compounds have also proven to be extremely effective bleaching activators. These compounds are water-soluble liquids.

Experiments have also shown that the peroxide in DF-200 formulations is also effectively activated by a nitrile-containing compound, such as 4-cyanobenzoic acid (which is water-soluble), at a concentration of, for example, 2%, for the neutralization of both chemical agent and biological agent simulants.

DF-200 Using Peracetic Acid

Tests were conducted using peracetic acid as the oxidant in DF-200, instead of hydrogen peroxide. The following formulation was used:

2% Variquat 80MC (cationic surfactant)
2% peracetic acid (oxidant)
5% potassium bicarbonate (buffer and activator)
91% water The pH was adjusted to 9.8 with solid KOH and the formulation was tested against the simulants for mustard, VX, and anthrax spores. The performance of this formulation is shown in Table 14 against chemical agent simulants.

TABLE 14

| Reaction rates in kinetic testing for DF-200 with 2% peracetic acid. | | | |
|---|---|---|---|
| | % Decontaminated | | |
| Simulant | 1 Minute | 15 Minutes | 60 Minutes |
| Mustard (HD) | 27 | 58 | 68 |
| VX | 68 | 76 | 95 |

Tests against the anthrax spore simulant (*Bacillus globigii* spores) demonstrated 99.9999% (7-Log) kill after a 30-minute exposure to DF-200 with 2% peracetic acid.

Tests were also conducted for DF-200 using a higher concentration of peracetic acid (3.5%) in the following formulation:

2% Variquat 80MC (cationic surfactant)
3.5% peracetic acid (oxidant)
5% potassium bicarbonate (buffer and activator)
89.5% water The pH was adjusted to 9.8 with solid KOH and the formulation was tested against the simulants for mustard, VX, and anthrax spores. The performance of this formulation is shown in Table 14 against chemical agent simulants.

TABLE 14

Reaction rates in kinetic testing for DF-200 with 3.5% peracetic acid.

| | % Decontaminated | | |
|---|---|---|---|
| Simulant | 1 Minute | 15 Minutes | 60 Minutes |
| Mustard (HD) | 40 | 94 | ND |
| VX | 74 | 96 | 98 |

The results show that use of peracetic acid as an alternative oxidant is effective against chemical agent simulants, but is not as effective as DF-200 formulations using activated hydrogen peroxide (i.e., the combination of hydrogen peroxide, bicarbonate, and propylene glycol diacetate) as the oxidant. However, the DF-200 formulations with 2-3.5% peracetic acid are very effective for spore kill. Nevertheless, use of this oxidant is not as attractive as hydrogen peroxide because peracetic acid is not presently available in a safe, convenient solid form, and the shelf life of the liquid form is rather short.

Tests were also conducted to determine the minimum constituents required for spore kill in a DF-200 formulation that utilizes peracetic acid as an oxidant. These results indicate that only three constituents, i.e., peracetic acid, bicarbonate and the cationic surfactant, are necessary to achieve high rates of spore kill.

Live Agent Tests Using DF-200HF

Live agent tests on three chemical agents (soman ("GD"), VX, and mustard ("HD")) and two biological agents (anthrax spores and *Yersinia pestis*) were conducted. The results of kinetic testing of DF-200HF (using a three-part configuration) on the chemical agents are shown in Table 15.

TABLE 15

Reaction rates in kinetic testing for DF-200HF against chemical agents.

| | % Destruction of Chemical Agent at Time Interval | | |
|---|---|---|---|
| Chemical Agent | 1 minute | 15 minutes | 60 minutes |
| GD | 99.98 ± 0.01 | 99.97 ± 0.01 | 99.98 ± 0.01 |
| VX | 91.20 ± 8.56 | 99.80 ± 0.08 | 99.88 ± 0.04 |
| HD | 78.13 ± 10.53 | 98.46 ± 1.43 | 99.84 ± 0.32 |

After exposure of GD to DF-200HF, methylphosphonic acid (MPA) and pinacolyl methylphosphonic acid (PMPA) were identified as byproducts. After exposure of VX to DF-200HF, ethyl methylphosphonic acid (EMPA) and MPA were identified as byproducts. This indicated that the destruction of the VX followed the more desirable path to the phosphonic acids, rather than to EA2192 (a toxic byproduct which can also be produced during VX degradation). Lastly, after exposure of HD to DF-200HF, the initial degradation products for HD comprised a mixture of the sulfoxide and sulfone byproducts, followed later by nearly complete disappearance of each of these byproducts after 60 minutes.

Results of tests against anthrax spores is shown in Tables 15 and 16 and against *Yersinia pestis* (i.e., the plague bacterium) are shown in Table 17 (NG refers to 'no growth'). The detection limit for these tests was 10 CFU/ml. Note that the 'error bars' in the '% Reduction' column takes into account this detection limit.

TABLE 15

Kill rates for *B. anthracis* AMES-RIID spores in a solution of DF-200HF.

| *B. anthracis* AMES-RID | Average CFU/ml | Log Reduction | % Reduction |
|---|---|---|---|
| Control | 1.21E + 07 | 0 | 0.00 |
| 15 min contact | NG | 7 | 100 ± .00004 |
| 30 min contact | NG | 7 | 100 ± .00004 |
| 60 min contact | NG | 7 | 100 ± .00004 |

TABLE 16

Kill rates for *B. anthracis* ANR-1 spores in a solution of DF-200HF.

| *B. anthracis* ANR-1 | Average CFU/ml | Log Reduction | % Reduction |
|---|---|---|---|
| Control | 6.42E + 07 | 0 | 0/00 |
| 15 min contact | NG | 7 | 100 ± .00004 |
| 30 min contact | NG | 7 | 100 ± .00004 |
| 60 min contact | NG | 7 | 100 ± .00004 |

TABLE 17

Kill rates for *Y. pestis* cells in a solution of DF-200HF.

| *Y. pestis* (ATCC 11953) | Average CFU/ml | Log Reduction | % Reduction |
|---|---|---|---|
| Control | 1.33E + 07 | 0 | 0.00 |
| 15 min contact | NG | 7 | 100 ± .00004 |
| 30 min contact | NG | 7 | 100 ± .00004 |
| 60 min contact | NG | 7 | 100 ± .00004 |

The Petri dishes used for cell growth on each of these tests were saved for 21 days following the tests to verify that DF-200HF had actually killed the spores, rather than just inhibiting their growth. No growth on any of the Petri dishes was observed after the 21-day period.

Another example of a DF-200 decontamination formulation is shown below.

Part A:

2 grams Variquat 80MC
1 gram Adogen
0.4 g 1-dodecanol
0.5 g isobutanol
0.8 g Diethylene glycol monobutyl ether (DEGMBE)
10 g propylene glycol
0.16 g celquat 240SC
4.5 g K carbonate
0.5 g K bicarbonate
30.1 g deionized water Part B:

43.3 g 8% liquid hydrogen peroxide

Part C:

2 grams diacetin

Recipe: To make Part A: Start with water, add K Garb and K Bicarb while stirring. After dissolution, add Celquat slowly while stirring. Stir for 15-30 minutes, longer if required to allow the Celquat to dissolve. Add PG, stir. Add Variquat and Adogen, stir. In separate vessel, mix isobutanol and dodecanol and DEGMBE. Add to Part A while stirring. To make DF-200, mix Parts A, B, and C together.

Modifications to DF-200 Formulations for Knockdown Spray Applications

Bench-scale experimental work was performed with investigation of modifications to the standard DF-200 technology related to agent solubility, freeze point depression and surface tension depression, in order to improve the efficiency and effective of sprayed DF-200 droplets for toxic cloud knockdown and neutralization. These elements were varied with the intent of increasing agent capture efficiency. Another characteristic important to efficient agent capture and solubility is evaporation depression, which may be achieved by increasing the organic concentration in the decontamination formula. To date, progress has been made in examining the use of alternative cationic surfactants, and adjusting solvents or co-solvents in the decontamination system.

The affects of these modifications have been measured by a series of solubility tests and surface tension measurements. The solubility tests were designed and chosen as a method of determining agent simulant solubility exclusively, without the concurrent use of stirring, heating, etc., techniques that would enhance the solubilization process. The chemical agent simulants subjected to this test included O,S-diethylphenylphosphonothioate, 2-chloroethyl ethyl sulfide and 2-chloroethyl phenyl sulfide, simulants for VX and mustard, respectively. The test commences with the addition of a drop of chemical agent simulant to a small test tube containing a modified DF-200 formulation. A series of events will occur as the simulant solubilizes in the formulation. For instance, the simulant bead is initially flat on the bottom of the test tube. The simulant bead becomes convex in form, begins to breakdown or separate and eventually these small droplets will rise to the top level of formulation. The simulant beads will eventually form a clear layer, and then as local solubilization occurs, no layer is visually present on the top formulation layer. These events are visually observed and the time of each event recorded.

Various modified DF-200 formulations were subjected to the solubility test. Results indicate expected variances in solubility among the different simulants. To date, both VX and mustard simulants have been most readily soluble in the standard DF-200. One modified formula demonstrated slightly improved VX simulant solubility relative to DF-200. Modifications tested thus far include changes in the primary solvent (i.e., diethylene glycol monobutyl ether was replaced with propylene glycol to increase cold temperature stability); use of alternate cationic surfactants with increased surface tension reduction or detergency capabilities; and use of an alternate fatty alcohol, added primarily for foam stability and agent solubility.

Formulations with demonstrated solubility and chemical agent simulant decon efficacy were evaluated for surface tension, with effort to reduce surface tension as a tactic in enhancing the aerosol capture efficiency.

We pursued the use of double-chained cationic surfactants, in particular double-chained quaternary ammonium compounds. These surfactants are reported to increase reaction rate constants. The presence of two cationic species in these surfactants increases the catalytic properties of the respective micelles. To date, we have not found a commercial supplier of this type of surfactant. We synthesized the compound because a commercial source was not identified. Efficacy results did not warrant further investigation of this surfactant.

Another cationic surfactant explored was Barquat 4280Z, which is a mix of alkyl dimethyl benzyl ammonium chlorides and alkyl dimethyl ethylbenzyl ammonium chlorides (i.e., "second generation" quaternary ammonium compounds) generally used against biological pathogens including algae, fungi, viruses and bacteria, including potent germicidal action in heavy and organic soil loads, in disinfectants, sanitizers and algaecides. The mixture of quaternary ammonium compounds is considered to provide synergistic effectiveness. Preliminary data from another ongoing project indicate that one particular mixed quat product performed favorably with regards to decontamination in a highly organic loaded environment, an indication of the surfactant's increased surface activity. This surfactant was used in modified formulations that were deployed in a limited number of tests conducted during the second year of the project. Additions of up to about 5% of a mix of alkyl dimethyl benzyl ammonium chlorides and alkyl dimethyl ethylbenzyl ammonium chlorides (i.e., "second generation" quaternary ammonium compounds) can be used in DF-200 formulations.

Another additive that we investigated was Q2-5211, manufactured by DOW Chemicals. This is a "superwetting agent" comprising a low viscosity silicone polyether liquid, which has a low surface energy and rapid spreading and wetting. Additions of up to about 5% of a superwetting agent can be used in DF-200 formulations. In summary, modifications of the decon formulation included investigation of alternative surfactants and selected solvents. Surface tension, chemical agent simulant solubility and decon efficacy were assessed with the ultimate goal the development of a formulation that demonstrates effective agent capture efficiency. Modified formulations have been developed which exhibit a decrease in surface tension (relative to standard DF-200) of ~30%; theoretically, this improvement should increase the agent capture efficiency. Modified formulations were evaluated in chamber tests conducted in FY'05.

Toxic Cloud Spray Knockdown Experiments

We have experimentally demonstrated increased agent simulant drop collection by the use of charged sprays emitted from electrostatic spray nozzles. Knockdown and neutralization of chemical agent simulants was evaluated by measuring chemical agent simulant concentrations in an aerosol test chamber immediately following release of well-characterized decontamination sprays. Data indicate a significant decrease in chemical simulant concentration, as expected.

Spray chamber tests, using appropriate chemical and biological agent simulants, were performed as required for modeling development, validation and calibration. Aerosol chamber testing commenced in August, 2004. Aerosol chamber test system parameters were optimized by December, 2004 Preliminary chamber testing indicated a knockdown and neutralization of chemical simulant agent concentrations ranging from one to four orders of magnitude (1-log to 4-log reductions). Results were collected following use of standard DF-200 deployed from ESS (electrostatic spray nozzles) in the charged state. Initial results suggested the potential efficiency of charged mitigation sprays in neutralizing aerosolized agents and aerosol chamber testing continued throughout the year. Using threat agent scenarios, Gaussian modeling was performed to predict agent plume exposure concentrations at 2, 5 and 10 Km downwind of an agent release. Peak plume exposure concentrations were then used as target simulant concentrations during aerosol test chamber testing.

Figure 2:
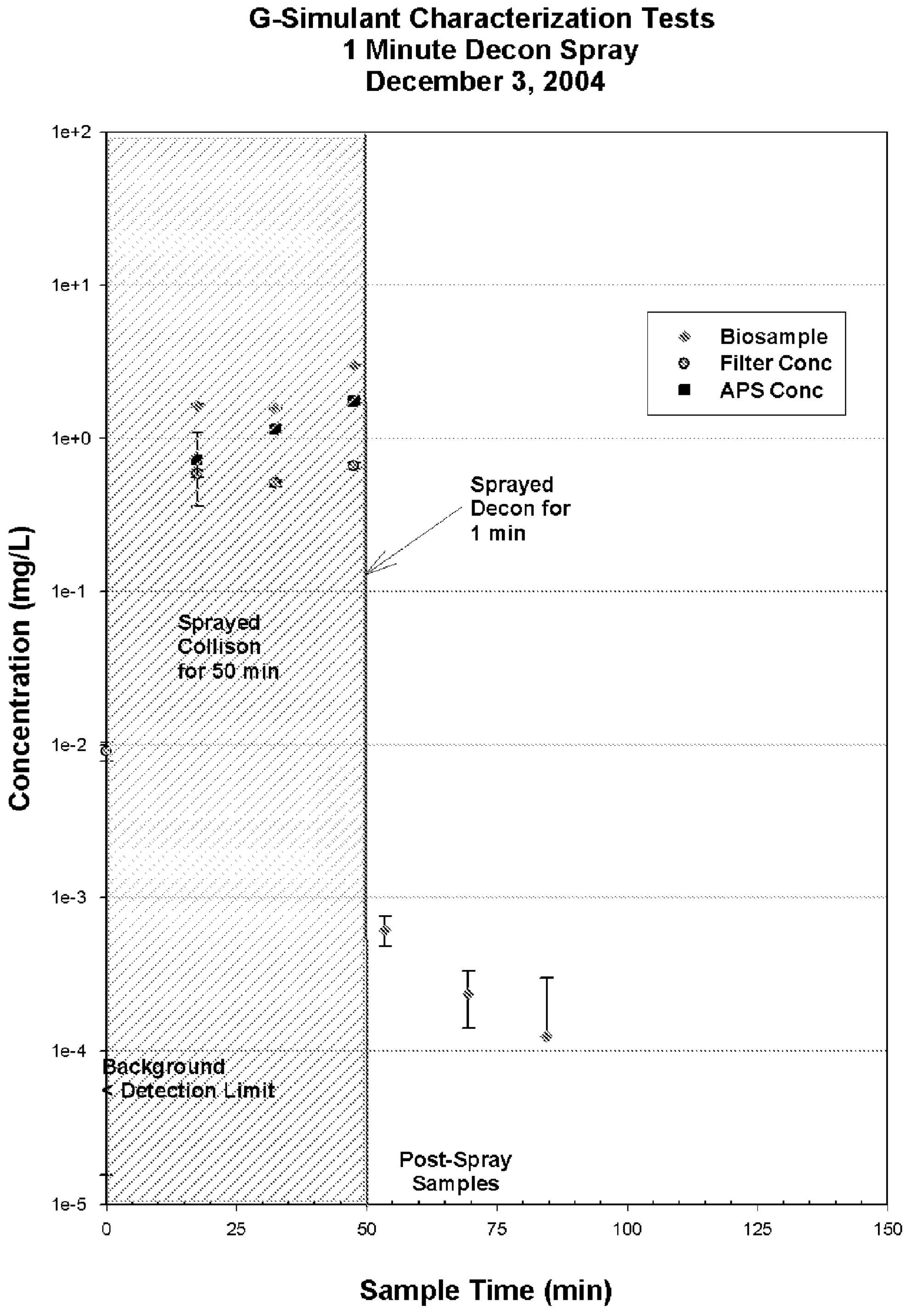
FIG. 2 shows a plot of the concentration of G-agent simulant, as a function of time, after being exposed to a 1-minute long spray of DF-200 decontamination solution.
Figure 3:
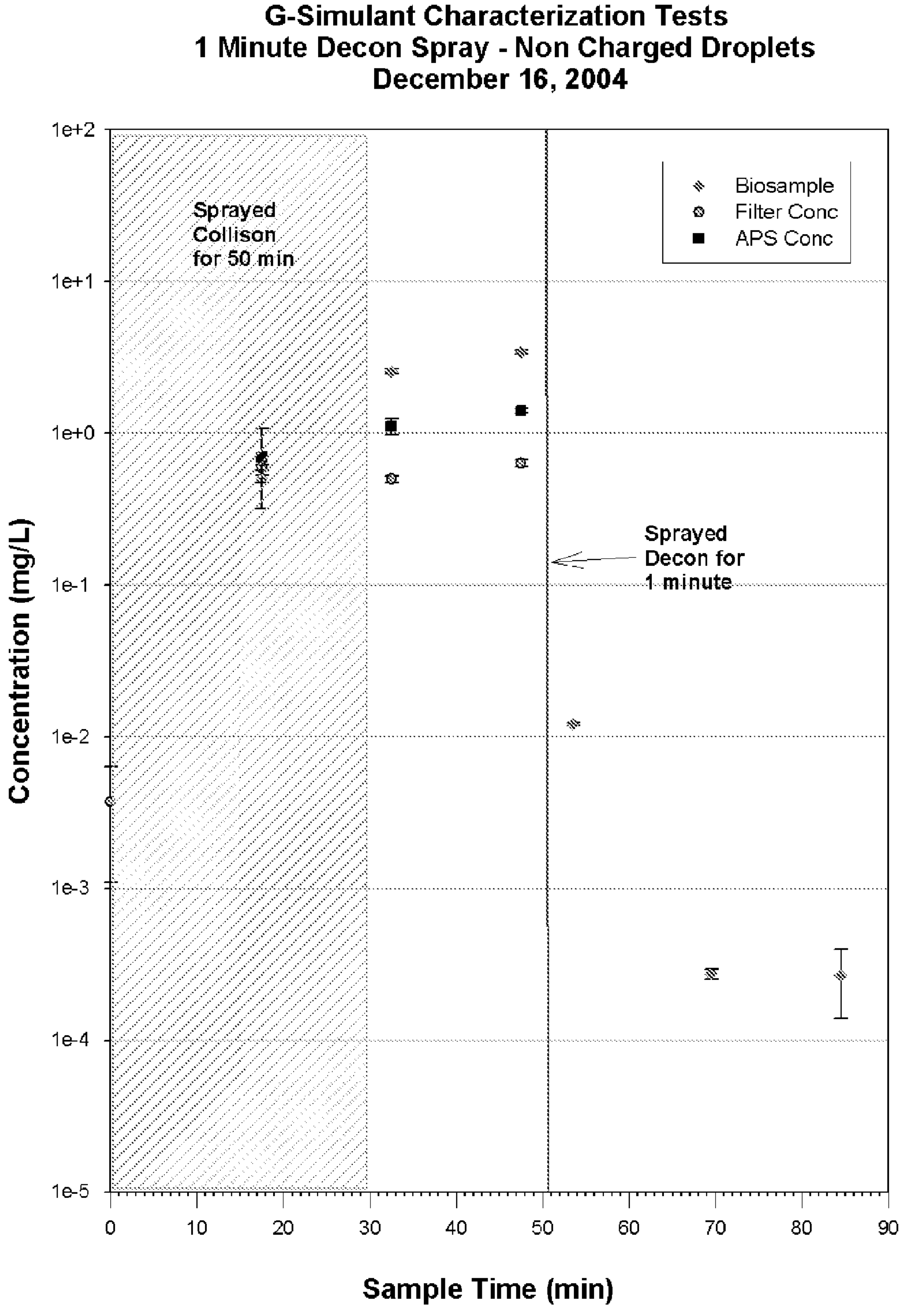
FIG. 3 shows a plot of the concentration of G-agent simulant, as a function of time, after being exposed to a 1-minute long spray of DF-200 decontamination solution, without charging the electrostatic nozzles.
Figure 4:
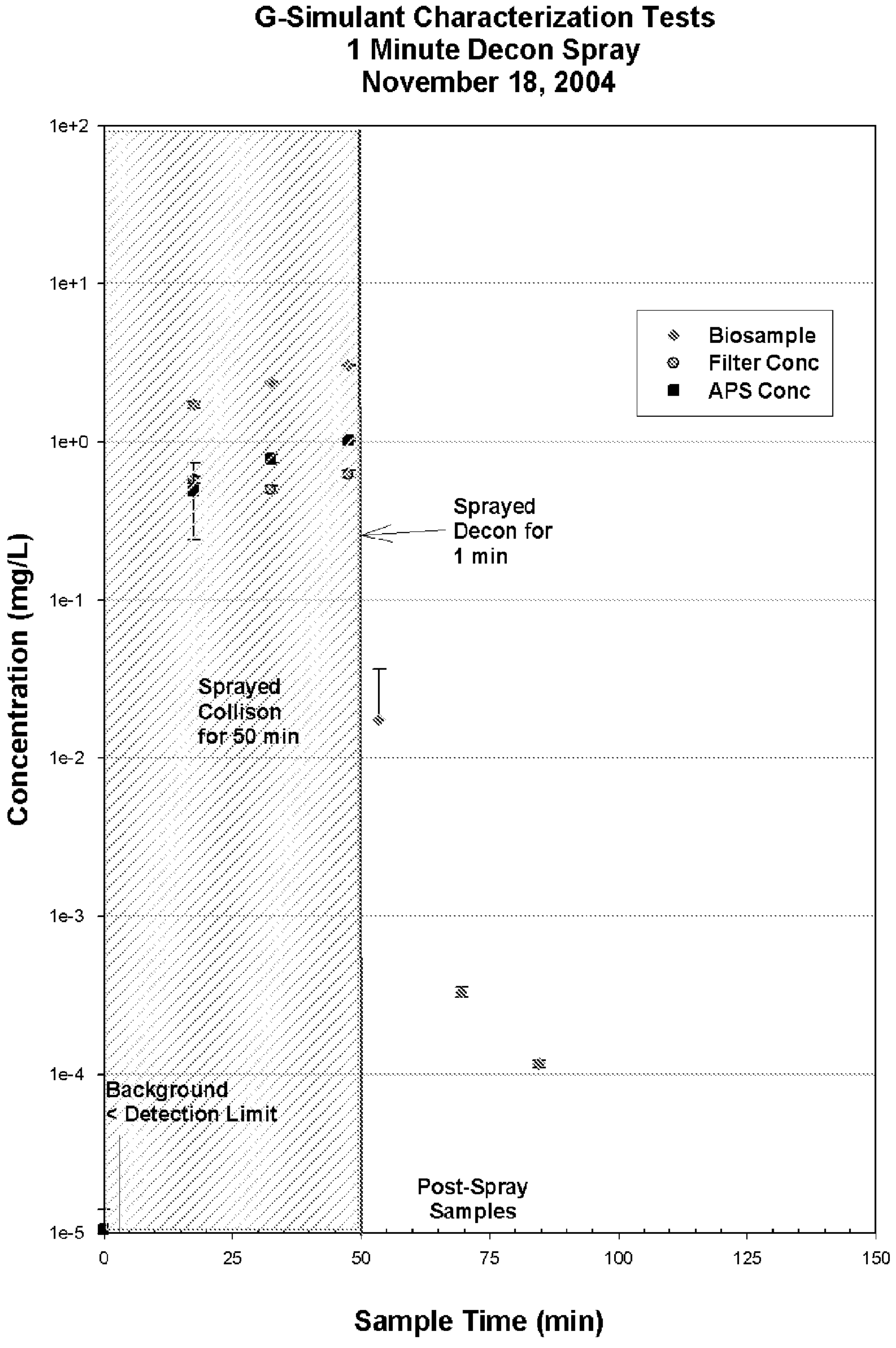
FIG. 4 shows a plot of the concentration of G-agent simulant, as a function of time, after being exposed to a 1-minute long spray of DF-200 decontamination solution.

In tests conducted at Sandia's Aerosol Test Chamber Facility, rapid and effective knockdown and neutralization of chemical and biological simulants was demonstrated. An aerosolized cloud of a G-agent stimulant (diphenyl chlorophosphate) was released at a concentration of 3.2 $g/m^3$ in an 8'×8'×8' test chamber. The cloud was well mixed by a series of fans in the test chamber for a period of 50 minutes, corresponding to simulant introduction into the chamber through the use of collision nebulizers. After the 50-minute simulant charge process, a spray of DF-200 was deployed for one minute through a series of nine ESS (Electrostatic Spray) spray nozzles that were located in an array at the top of the test chamber (the air pressure supplied to the nozzles was approximately 80 psig). The total volume of DF-200 spray deployed in the chamber was 2 L and the concentration of DF-200 in the chamber was approximately 138 $g/m^3$ making the challenge ratio (decon:stimulant) approximately 40:1. The G-agent simulant was collected by aerosol sampling and the simulant concentration in the chamber was determined by gas chromatography immediately after the end of the spray period and again at 15 and 30 minutes after the end of the spray period. The results, some examples of which are shown in FIGS. 2-4, demonstrate nearly 4 log knock-down and neutralization of the stimulant immediately after the spray was stopped. This decrease in agent simulant concentration is in excess of the 1.5-2 orders of magnitude decrease required to bring potential chemical agent exposures (as determined by Gaussian modeling of potential threat scenarios) below the $LCt_{50}$. As a comparison, starting with nearly two orders of magnitude greater surrogate concentration, current data indicate approximately four orders of knockdown and neutralization of the G-agent surrogate accomplished using 90% less formulation (relative to test data conducted under the DARPA Immune Building Program, 2001-2002).

Figure 5:
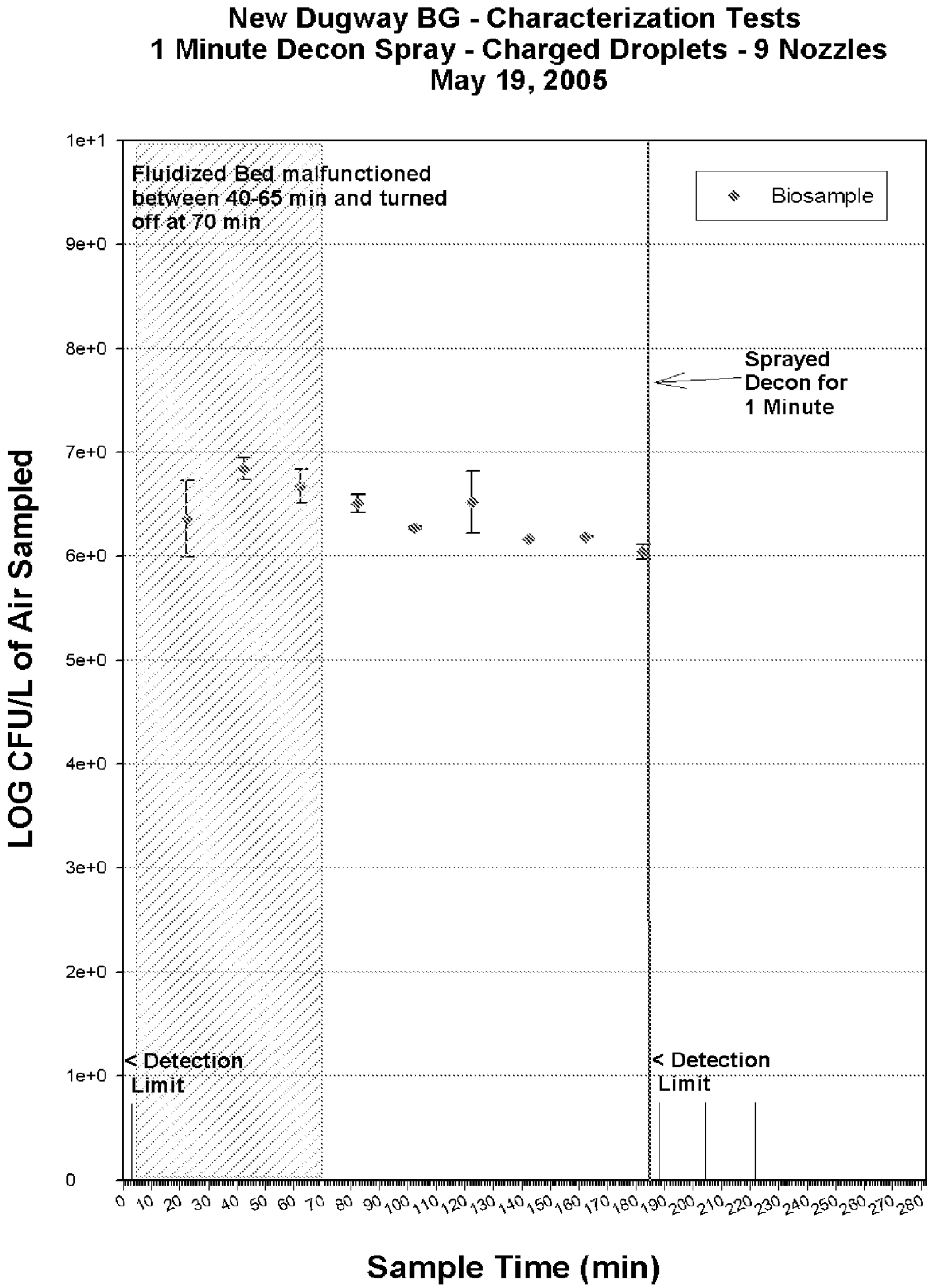
FIG. 5 shows a plot of the concentration of New Dugway BG simulant, as a function of time, after being exposed to a 1-minute long spray of DF-200 decontamination solution.

Using a similar test matrix, knockdown and neutralization of *Bacillus globigii* (*atrophaeus*), surrogate for anthrax was also demonstrated. Initial chamber aerosol samples were determined to contain 5.1 LOG CFU/L of *B. atrophaeus. B. atrophaeus* was not detected immediately after and 15 minutes following a 1 minute charged DF-200 spray, indicating a knockdown and neutralization of greater than 5 orders of magnitude. A decrease in 4 orders of magnitude is required to bring biological agent peak exposure concentration (as determined by Gaussian plume modeling) below the $ICt_{50}$. Additional testing using a charged DF-200 spray density of 92 $g/m^3$ demonstrated a 5 LOG knockdown and neutralization of the anthrax simulant; a 46 $g/m^3$ charged DF-200 spray density demonstrated 4 LOG immediate knockdown and neutralization. A typical knockdown response of New Dugway BG simulant is shown in FIG. 5.

During the second half of the second year, experimental efforts were directed at knockdown and neutralization of various agent threats and assessing variables to the spray system such as ESS nozzle charge, spray droplet size, decontamination formula and spray duration. A detailed summary of chemical agent simulant aerosol test protocol is described in the following narrative.

Purpose: To determine the effectiveness of cloud dispersal of Sandia decontamination formulations on a chemical agent simulant released by an aerosol dispersion.

Materials:

Chemical Agent Stimulants:

G-Agent Diphenyl chlorophosphate 99% (CAS#2524-64-3)

Mustard 2-Chloroethyl ethyl sulfide 98% (CAS#693-07-2)

Mustard 2-Chloroethyl phenyl sulfide 98% (CAS#5535-49-9)

Quenching Solvents (Depending on Agent Simulant)

Acetonitrile—ACS grade

Methanol—ACS grade

Agilent Gas Chromatography (6890) with FPD (flame photoionization detector)

Electrostatic Spray Nozzles

Compressed Air cylinder with appropriate regulators

SKC biosamplers, 20 mL, SKC Catalog #225-9595

Analytical balance, Mettler M120—Note—all weights were collected to four decimal places, 0.0001 gram.

Method and Analysis:

Chemical agent simulants were selected to have chemical characteristics similar to that of the live threat agents. Gas chromatography methods utilizing a flame photoionization detector with appropriate lens were developed to determine the concentration of chemical agent simulant in an aerosol sample volume. Prior to testing, standards for the specific agent simulant were injected on the GC instrument. The respective responses were then used to generate concentration curves for each agent simulant. For each agent simulant a minimum of two standard curves (based on injection methodology) were generated, a pulse and a split curve, generating analysis methods with valid detection ranging from 0.1 to 3000 μg/mL depending on the agent.

The pulse curve is a more sensitive method with valid detection ranging from 0.1 to 80 μg/mL, depending on the agent. A pulse method's general operation is to load additional sample onto the chromatographic column (using a higher pressure pulse injection) so that the instrumentation is able to give better resolution in lower concentrations. The split curve methods had valid detection ranging from 30 to 3000 μg/mL, depending on the agent. The split curve methodology functions by splitting away a portion of the sample to a vent line so as to dilute the sample during loading onto the column. This allows higher concentrations to be run on the instrument without overloading the detector. On test days GC check standards are run prior to the test and after the last sample runs.

Aerosol Sampling

Aerosol sampling of the aerosol test chamber atmosphere utilized SKC biosamplers and a solvent that would effectively "quench" the simulant. More importantly it had shown effective at quenching the neutralization reaction of the decontamination solution and the simulant. Test data was collected gravimetrically so as to reduce any errors that might be associated with use of adjustable volume pipettes with solvents. Gravimetric data also allowed determination of exact volumes remaining in biosamplers post-sample collection without disturbing the sample, since there was solvent loss that occurred during aerosol sample collection due to evaporation.

Initial weights of the biosampler collection vessel and lid were recorded for each sample. Next, 20 mL of solvent was placed in each vessel and recapped. After each aerosol sample was collected a post weight was also recorded. Then dilutions were done in GC autosampler vials by taking weights of empty GC vial with cap. Weight with dilution solvent was recorded, if needed and sample aliquots were added and total masses recorded. Sample was then capped and mixed before placing in GC autosampler tray.

Initial aerosol chamber testing included the performance of a decay assessment for each simulant. The purposes of the simulant decay tests were 1) to determine the amount of time required to fill the test facility's chamber with maximum, or target threat concentration; and 2) to monitor the potential natural fallout of simulant particles or vapor over time. These allowed us to determine charging time of the chamber, and through the use of particle size sampling equipment, to determine particle size distribution and when particle concentrations started to decrease, inferring saturation of the air volume. These tests provided guidance in determining test matrix for later tests.

The general aerosol test process is described as follows: Prior to loading the simulant into the chamber a background aerosol sample was collected and analyzed on pulse method to confirm a "clean" starting condition. Simulant was introduced into the chamber until concentrations correlating to peak agent plume exposure (as determined by Gaussian modeling) were achieved. Initial testing of each simulant also required the performance of decay assessments, described above. During the simulant charging process, aerosol samples were collected periodically. At a pre-determined time, the charged DF-200 spray was deployed for 1-minute duration. Aerosol sampling commenced immediately after the completion of the 1-minute mitigation spray, again at 15 and 30 minutes later. General sampling plans encompassed the following 5 minute aerosol samples:

- Background
- Pre-decontamination spray (at minimum the last 5 minutes before spray, typically there were between 2 and 4 sample periods before decontamination spray deployment).
- Post decontamination spray (immediately after spray (0 minutes), 15 minutes after spray finished (15 minute), and 30 minutes after the termination of spraying (30 minute)

Follow-on testing also evaluated the knockdown and neutralization efficiency using various simulant and/or charged decontamination spray densities.

Post-charged decontamination spray solution aerosol samples were always run as close to sample completion as possible, i.e., diluted and injected onto the GC as soon as possible. This equates to being injected typically within 10 minutes of collection. All individual sample vials were injected once; and then a second injection from each vial was made before injecting the pre-decontamination solution samples. Typically post samples were analyzed utilizing pulse injection methodology and pre samples were always analyzed utilizing split injection methodology.

Weight and chromatogram response results data were then entered into an Excel spreadsheet to determine concentration levels taking dilutions into account and also biosampler air volumes. Additional aerosol data was collected utilizing an Aerodynamic Particle Sizer (APS) particle monitoring instrumentation prior to decontamination solution. Nozzle liquid flow rate, nozzle flow pressure, chamber pressure and temperature were recorded throughout the tests with electronic flow and pressure sensors and thermocouples. This data aided in the correlation of data between tests.

Test parameters that were varied included: charged nozzles vs. uncharged nozzles, duration of decontaminant spray, flow rate of spray (and thus, droplet size), compressed air source vs. house air, and decontaminant formulation.

Protocol for Knockdown and Neutralization of Biological Simulants

A detailed summary of biological agent simulant aerosol test protocol is described in the following narrative.

Purpose:

To utilize the Aerosol Test Facility to test various government agency threat scenarios of aerosolized biological simulant and to determine the effectiveness of Sandia developed decontamination formulations against the aerosolized biological simulant.

Materials:

SKC BioSampler™
Swag-Lock end caps
Bleach
Fluidized Bed Generator
Aerosol Test Chamber
Particle monitoring instrumentation (APS)
Neutralizer solution
Bovine Liver Catalase (1% solution)
Sterile De-ionized water
Pipette and pipette tips (sterilized)
*Bacillus globigii* spores; dry powder (Dugway Proving Ground)
Brain Heart Infusion Agar (Difco)
115×25 Sterile Petri Dishes
3M™ PetriFilm Aerobic Count Plates
Autoclave
Test Tubes
Test Tube caps
Test Tube racks
Autoclave waste bags and tape
Water bath
Ultrasonic water bath
Vortexer Method:

Aerosol Test Facility-Pre-Test Cleaning/Sampling

Prior to starting a test, the aerosol sampling lines are cleaned using a 10% bleach solution and a scrub brush of appropriate size. The bleach solution was sprayed through the exterior bulk head connections on the test chamber's west wall through the stainless steel plumbing. The bleach was sprayed until solution was visible exiting from the plumbing in the interior of the chamber. Solution was allowed to sit in the stainless steel lines for a minimum of 10 minutes, then the scrub brush was employed to ream out the interior of the lines and allowed to sit another 10 minutes. De-ionized water was then used to rinse the bleach out of the lines. The lines were then air dried for approximately 30 minutes before beginning the pre-test sampling.

After cleaning the aerosol sampling lines, swab samples of each aerosol sampling line orifice were collected, using sterile swabs and sterile Butterfield's Buffer water. For each sample line there was a 50 mL pre-sterile conical tube (Corning) with 30 mL Butterfield's Buffer. A sterile swab was moistened by dipping it into the tube. The swab was then inserted into the orifice swabbing the interior of the line in a corkscrew fashion. A separate swab was used for interior and exterior orifice sampling. However; both swabs were placed in the same conical tube.

Aerosol Test Facility-Aerosol Sample Collection

A background aerosol sample was collected of the test chamber atmosphere prior to addition of aerosolized *Bacillus globigii* (*B. anthracis* stimulant). After the background sample was collected, the fluidized bed generator was turned on and the valve into the test chamber was opened, allowing flow of simulant into the test chamber. The interval between collections of aerosol samples was determined prior to the test start.

After aerosol samples were collected the BioSampler™(s) were removed. A 1 mL sample was removed and placed into 9 mL of neutralizer solution (8.9 mL Neutralizer+0.1 mL 1% Bovine liver catalase). Catalase solution was kept cool prior to adding it to the Neutralizer. Catalase was added to neutralizer within 5 minutes of the sample being added. Sample was then agitated to ensure that all components interact. The remainder of sample was discarded in bleach solution.

All components of the BioSampler™(s) were cleaned between sample collections by soaking in a 25-50% bleach solution for a minimum of 4 minutes. The samplers were then rinsed a minimum of four times in de-ionized water, and dried by paper towel, shaking, and then flushed with canned air. Canned air was sprayed into each orifice of the sampler to ensure there was no clogging within the nozzles.

After reaching a pre-determined concentration (predicted agent plume exposure concentration determined by Gaussian modeling of potential threat scenarios) the fluidized bed was turned off and the ball valve to the chamber was closed. If a decay test was being performed then additional samples are taken over a time frame to determine fall-out of the simulant. Both after a decay test and when a decay test is not being performed, decontamination solution (EFT DF-200) was deployed into the chamber using a pre-determined set of parameters (i.e. spray duration, number of nozzles, nozzle pressure, and charged/uncharged nozzles). After deployment of the decontamination spray the chamber was immediately sampled as described above. Samples were then collected at increments thereafter to determine effectiveness of the decontamination spray over time. When all samples were collected the remaining decontamination was deployed into the chamber followed by de-ionized water (approximately 3 gallons). EFT EasyDecon parts A, B, and C were combined less then 15 minutes prior to deployment. Cylinders of UHP grade Compressed Air were used to deploy the decontamination solution so that a constant, high flow (required for optimal small droplet size) could be achieved.

Initially, aerosol sample collection of post-decontamination samples was altered by pouring the complete BioSampler™ contents (20 mL) into 180 mL of neutralizer solution. After initial testing with this methodology, it was determined that the high dilution factor was detracting from the goal. It was determined that the neutralizer solution effectively quenches the reaction of the DF-200 at a 1:1 ratio (this is a conservative value as the actual decontamination solution in Biosampler™ is diluted by 20 mL of De-ionized water). Later tests used the 1:1 (20 mL Neutralizer:20 mL aerosol sample) ratio for post decontamination sample collection. This was done to minimize the dilution factor used in post-test calculations, thus increasing the sensitivity of the analyses. All waste generated in this process was autoclaved and disposed of via appropriate waste streams.

Building 823—Plating

All samples were transported from the TA3 aerosol test facility to Building 823 for subsequent processing. Liquid samples were heat shocked in 65° C. water bath for one hour prior to plating; swab samples were sonicated for 15 minutes prior to heat shocking. The purpose of heat shocking was to kill all vegetative cells, a step required because the 3M Petrifilm™ enumeration material is sensitive for total aerobic microorganisms, thus not selective for *Bacillus globigii*. The pre-decontamination samples were enumerated on 3 MPetrifilm™ Aerobic Count Plates and the post-decontamination samples were enumerated on both 3 MPetrifilm™ Aerobic Count Plates as well as Brain Heart Infusion agar (Difco) using pour plate technique. A single set of serial dilutions were used with each sample plated in triplicate to ensure better statistical data.

All plates were incubated at 37° C. for 48-hours. Plates with counts less then 30 colony forming units (CFU) or greater than 300 CFU were not used due to the methodology limits at those extremes. Plates were autoclaved after counting and disposed of via appropriate waste stream. Results for each test were reported as CFU per milliliter of sample in an Excel spreadsheet. These results were further reported as CFU per L of Air Sampled. See Appendix A for all results of biological simulant knockdown and kill efficacy using DF-200 charged mitigation spray.

Problems encountered during this phase of the experimental project include inefficient operation of the charged nozzles, due to corrosion of the electrodes within the nozzle cavity. This was remedied by removing the nozzle head covers after testing and thoroughly rinsing the electrodes within the nozzle cavity. The covers were not reinstalled until immediately prior to the next test. Additionally, prior to each test, the charge on each nozzle was determined to be efficient operational by measurement with an electrometer. Nozzles were optimally operated at −1600 V.

Correlation Between APS and Plating Enumeration Methods

An important component of the aerosol test chamber testing capability is the measurement of particle size and distribution using the Aerodynamic Particle Sizer (APS) instrumentation. A correlation study was performed to assess the performance of the APS relative to enumeration of BioSampler constituents. Over the concentration range evaluated, there was general consistent correlation between the two methods with acceptable variance between most data points.

Assessment was performed of various CBW cloud knockdown and decontamination deployment systems for force protection at a stand-alone facility such as an airbase. Knockdown approaches considered include ground-based knockdown systems; fan assisted systems and aircraft knockdown. Optimum knockdown approaches for specific applications for subway protection and chemical demilitarization are presented based on feasibility and efficiency of achieving cloud knockdown and decontamination.

In a live-agent threat scenario, a conceptual model of aerosolized cloud knockdown and neutralization is presented as follows: Consider an area defined for protection, either indoor or outdoor. Upon detection of an incoming CBW agent cloud, a series of telescoping towers (or other mobile deployment device) could be engaged at various elevations and perpendicular to the plume, thus providing an effective spray curtain of optimized decontaminant droplet charge, size and concentration. For outdoor applications, the plume motion itself would produce the means to mix the neutralizing spray drops into the agent plume so that the facilities and people downwind of the dispersion location would be exposed to a neutralized plume, thus providing a region of safety downwind of the agent dispersal. The spray deployment devices may either remain at fixed locations, or be mobile, allowing their transport to protect different areas of primary interest. For indoor applications, upon activation by either an automatic sensor or manual button, a mitigation spray nozzle system could be engaged immediately deploying the optimized charged droplet decontaminant solution. Mixing could be optimized by use of fans and/or strategic operation of the HVAC system.

As an example of a mobile, outdoor protection deployment concept, the Falcon unit, manufactured by Intelegard, Inc., could be either retrofitted or manufactured with an optimized charged spray mitigation nozzle system. The Falcon unit is a 3-ton truck with a commercial trailer that accommodates a compressed air-driven foam generator with three different types of specialized nozzles for deploying DF-200 foam. The current load capacity of the trailer is 500 gallons of DF-200 solution. Several hundred Falcon units have been procured and fielded in Afghanistan and the Middle East by the US Military, thus the Falcon is readily available for modification and rapid, mobile deployment options. A Falcon unit retrofitted with a charged spray mitigation nozzle system would be ideal for protection of relatively small areas, such as a few aircraft on an airfield or a group of tanks in the battlefield. It would thus be an accessible, effective solution for mobile, fixed site decontamination and protection using charged mitigation sprays.

Proof of concept in knockdown and neutralization of aerosolized CBW agent simulant clouds was demonstrated during the performance of this project. Particularly effective was the knockdown and neutralization of *Bacillus globigii*, a simulant for anthrax. Decreases of 5 orders of magnitude in anthrax simulant was demonstrated using both high (138 g/m$^3$) and intermediate charged DF-200 spray densities (92 g/m$^3$). At the low charged DF-200 spray density of 46 g/m$^3$, 4-log decrease in anthrax simulant was observed. All observed results (see, for example, FIG. 5) indicate that charged mitigation sprays would sufficiently lower predicted peak biological agent plume exposures to levels below the $ICt_{50}$, the inhalation exposure dose lethal to 50% of the military population. It should be noted that in the tests performed at the lowest spray density, although growth was not detected in the aerosol samples collected immediately after the 1-minute charged spray, a rebound effect was noted, i.e., Colony Forming Units (CFU) were observed during post-test pour plate enumeration of 15 and 30 minute aerosol samples. However, the observed CFU counts were primarily in the range of 1-10, well below the reliable detection limit of the enumeration method (30-300 CFU per plate); most of the reported counts were 0 CFU. The noted tests were conducted on June 2, June 20 and Jun. 21, 2005. The rebound effect, although technically insignificant, was inversely related to the spray density. The greatest rebound was observed at the lowest spray density. This noted, insignificant trend was more apparent in the BHI pour plates, as compared to the PetriFilm™ method, suggesting the BHI pour plate method may be more sensitive under the test conditions.

Results were also highly promising for effective knockdown and neutralization of the G-agent simulant by use of charged DF-200 mitigation sprays. Results indicate charged mitigation sprays would sufficiently lower predicted peak chemical G-agent exposures to levels below the $LD_{50}$, using a spray density of 138 $g/m^3$. Evaluation of chemical agent simulant knockdown and neutralization using lower spray densities was not accomplished before the end of the project. Of significance is the observation that effective knockdown and neutralization as noted above was achieved using threat scenarios and challenges of an exceedingly high nature. Typical G-simulant knockdown response plots are shown in FIGS. 3-5.

The results for the mustard agent simulants demonstrated decreases in aerosol concentration ranging from between one to two orders of magnitude. Attempts to increase the charged spray efficacy utilized longer spray durations and repeated sprays, and decreased simulant concentration. Clearly, there are factors involving agent/decontaminant material solubility, and decontaminant material droplet size and charge that need to be investigated further in order to accomplish effective knockdown and neutralization of mustard simulants. APS data indicated that the mustard simulants were dispersed as smaller particles or vapors, as compared to the G-agent simulant. Suggested future experiments would address decontaminant/agent solubility and improvements to the mitigation spray nozzle that would allow deployment of smaller charged spray droplets. Additionally, the charge is another factor that could be altered.

Modified formulations were tested on the following dates: Oct. 21, 27, and 28, 2004; Jan. 13 and 14, 2005. As described above, tests performed prior to December 2004 were performed under non-optimized test parameters. The spray duration and charged droplet size were not optimized until the December, 2004 timeframe. The results of the modified formulation tests in October were not as favorable as those achieved later in the test program, demonstrating a G-agent simulant concentration decrease of less than two orders of magnitude. The tests performed in January, after the hardware optimization was achieved, were more favorable. The initial rate of capture and neutralization was slower than with the charged DF-200 sprays. However, at 30 minutes following charged spray deployment, the simulant was not detected in any of the aerosol test samples. Thus, using charged, modified DF-200 formulation, the rate of neutralization was higher with increased test duration.

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A method of decontaminating cloud of toxic material, comprising:

generating a co-dispersion of two different droplet size distributions of negatively-charged droplets of DF-200 aqueous decontamination formulation; and contacting and chemically reacting the DF-200 droplets with the cloud of toxic material to neutralize and render the toxic cloud harmless;

wherein the DF-200 aqueous decontamination formulation comprises:

a solubilizing agent selected from the group consisting of a cationic surfactant, a cationic hydrotrope, and a fatty alcohol;

a reactive compound selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;

a bleaching activator selected from the group consisting of O-acetyl, N-acetyl, and nitrile group bleaching activators; and water; and wherein the co-dispersion comprises two different drop size distributions; (1) a small droplet size distribution, and (2) a large droplet size distribution;

wherein the small droplet size distribution is chosen to provide optimum neutralization of the toxic material, and the large droplet size distribution is chosen to hasten the fallout of the small droplets;

wherein generating the co-dispersion of the two different droplet size distributions comprises spraying the DF-200 formulation through two different size spray nozzles that are positioned side-by-side;

wherein the small droplet size distribution has a mean size that ranges from 1 to 20 microns; and wherein the large droplet size distribution has a mean size that ranges from 10 to 100 microns.

2. The method of claim 1, wherein the concentration of DF-200 sprayed into the toxic cloud is about 50 to 150 $g/m^3$.

3. The method of claim 1, wherein the duration of spraying the DF-200 formulation is about 1 minute.

4. The method of claim 1, wherein the DF-200 droplet size is 10 to 100 microns.

5. The method of claim 4, wherein the DF-200 droplet size is about 30-40 microns.

6. The method of claim 1, wherein the DF-200 droplets are sprayed from an electrostatic induction spray nozzle operating with an applied voltage of about 1500 to 2000 Volts: with an air pressure of about 80 to 100 psi, and with a DF-200 liquid flow rate of about 200 to 250 mL/minute (per nozzle).

7. The method of claim 1, wherein the DF-200 decontamination formulation has a pH value between about 9.6 and 9.8.

8. The method of claim 1, wherein the cationic surfactant in the DF-200 formulation comprises a quaternary ammonium salt selected from the group consisting of cetyltrimethyl ammonium bromide, benzalkonium chloride, benzethonium chloride, cetylpyridinium chloride, alkyldimethylbenzylammonium salt, tetrabutyl ammonium bromide, and a mixture of benzyl (C12-C16) alkyldimethylammonium chlorides, and combinations thereof.

9. The method of claim 1, wherein the DF-200 decontamination formulation further comprises a water-soluble polymer.

10. The method of claim 9, wherein the water-soluble polymer is selected from the group consisting of polyvinyl alcohol, guar gum, (cationic or non-ionic) polydiallyl dimethyl ammonium chloride, polyacrylamide, poly(ethylene oxide), glycerol, polyethylene glycol 8000 (PEG 8000), Guar Gum 2-hydroxypropyl ether, and polyquaternium-10, and combinations thereof.

11. The method of claim 1, wherein the DF-200 decontamination formulation further comprises a fatty alcohol comprising from 8 to 20 carbon atoms per molecule.

12. The method of claim 1, wherein the DF-200 decontamination formulation further comprises a solvent.

13. The method of claim 12, wherein the solvent comprises a member of the group consisting of propylene glycol, Di(propylene glycol) methyl ether, and diethylene glycol monobutyl ether, and combinations thereof.

14. The method of claim 1, wherein the DF-200 decontamination formulation further comprises a carbonate salt.

15. The method of claim 14, wherein the carbonate salt is selected from the group consisting of potassium bicarbonate, sodium bicarbonate, ammonium bicarbonate, ammonium hydrogen bicarbonate, lithium bicarbonate, ammonium carbonate, and potassium carbonate, and combinations thereof.

16. The method of claim 1, wherein the bleaching activator is water-soluble.

17. The method of claim 16, wherein said at least one water-soluble bleaching activator is selected from the group consisting of acetylcholine chloride, monoacetin (glycerol monoacetate), diacetin (glycerol diacetate), 4-cyanobenzoic acid, ethylene glycol diacetate, propylene glycol monomethyl ether acetate, methyl acetate, dimethyl glutarate, diethylene glycol monoethyl ether acetate, glycerol monoacetate, glycerol triacetate and propylene glycol diacetate, and combinations thereof.

18. The method of claim 1, wherein the DF-200 decontamination formulation comprises a cationic hydrotrope.

19. The method of claim 1, wherein the DF-200 decontamination formulation further comprises propylene glycol as a freeze-point depressant.

20. The method of claim 1, wherein the DF-200 decontamination formulation further comprises a corrosion inhibitor selected from the group consisting of N,N-dimethyl ethanolamine; triethanolamine; ethanolamine salts of C9, C10, and C12 diacid mixtures; dicyclohexyl amine nitrite; and N,N-dibenzylamine.

21. The method of claim 1, wherein the ratio of the concentration of sprayed droplets of DF-200 aqueous decontamination formulation ($g/m^3$) to the concentration of the toxic material in the toxic cloud ($g/m^3$) is at least 40:1.

22. The method of claim 1, further comprising pre-mixing individual components of DF-200 to make a made-up solution of DF-200, prior to supplying the made-up solution to a spray nozzle for spraying.

23. The method of claim 1, wherein the DF-200 aqueous decontamination formulation comprises:
2-6% cationic surfactant,
2-6% sodium bicarbonate,
1-4% sodium carbonate,
1-10% propylene glycol,
1-5% silicone polyether liquid,
0.1-2% KOH,
1-5% diacetin,
1-8% hydrogen peroxide, and
remainder water.

24. The method of claim 23, wherein the formulation comprises:
3% cationic surfactant,
3% sodium bicarbonate,
2% sodium carbonate,
8% propylene glycol,
2% silicone polyether liquid,
1.5% KOH,
2% diacetin,
4% hydrogen peroxide, and
remainder water.

25. The method of claim 23, wherein the cationic surfactant comprises a mix of alkyl dimethyl benzyl ammonium chlorides and alkyl dimethyl ethylbenzyl ammonium chlorides.

26. The method of claim 1, wherein the small droplet size distribution has a mean size that ranges from 1 to 10 microns.

27. A method of decontaminating a cloud of toxic material, comprising:

generating a co-dispersion of two different droplet size distributions of negatively-charged droplets of DF-200 aqueous decontamination formulation and contacting and chemically reacting the DF-200 droplets with the cloud of toxic material to neutralize and render the toxic cloud harmless;

wherein the DF-200 aqueous decontamination formulation comprises:

a solubilizing agent selected from the group consisting of a cationic surfactant, a cationic hydrotrope, and a fatty alcohol;

a reactive compound selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;

a bleaching activator selected from the group consisting of O-acetyl, N-acetyl, and nitrile group bleaching activators; and water; and wherein the co-dispersion comprises two different drop size distributions: (1) a small droplet size distribution, and (2) a large droplet size distribution;

wherein the small droplet size distribution is chosen to provide optimum neutralization of the toxic material, and the large droplet size distribution is chosen to hasten the fallout of the small droplets;

wherein generating the co-dispersion of the two different droplet distributions comprises spraying the DF-200 formulation through two different size spray nozzles that are positioned side-by-side;

wherein the DF-200 droplets are sprayed from an elevated platform selected from the group consisting of a tower, a balloon, a cherry picker, and a mobile orchard sprayer.

28. A method of decontaminating a cloud of toxic material, comprising:

generating, with a single nozzle, negatively-charged droplets of DF-200 aqueous decontamination formulation; and contacting and chemically reacting the DF-200 droplets with the cloud of toxic material to neutralize and render the toxic cloud harmless;

wherein the DF-200 aqueous decontamination formulation comprises:

a solubilizing agent selected from the group consisting of a cationic surfactant, a cationic hydrotrope, and a fatty alcohol;

a reactive compound selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;

a bleaching activator selected from the group consisting of O-acetyl, N-acetyl, and nitrile group bleaching activators; and water; and wherein generating the droplets comprises spraying the DF-200 formulation through said single nozzle at a high pressure, to generate droplets having a small droplet size distribution; and wherein generating the droplets also comprises spraying the DF-200 formulation through the same said single nozzle at a low pressure, to generate droplets having a large droplet size distribution; and wherein the small droplet size distribution is chosen to provide optimum neutralization of the toxic material, and the large droplet size distribution is chosen to hasten the fallout of the small droplets;

wherein the small droplet size distribution has a mean size that ranges from 1 to 20 microns; and wherein the large droplet size distribution has a mean size that ranges from 10 to 100 microns.

29. The method of claim 28, wherein the small droplet size distribution has a mean size that ranges from 1 to 10 microns.

30. A method of decontaminating a cloud of toxic material, comprising:

generating a co-dispersion of two different droplet size distributions of negatively-charged droplets of DF-200 aqueous decontamination formulation; and contacting and chemically reacting the DF-200 droplets with the cloud of toxic material to neutralize and render the toxic cloud harmless;

wherein the DF-200 aqueous decontamination formulation comprises:

a solubilizing agent selected from the group consisting of a cationic surfactant, a cationic hydrotrope, and a fatty alcohol;

a reactive compound selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;

a bleaching activator selected from the group consisting of O-acetyl, N-acetyl, and nitrile group bleaching activators; and water; and wherein the co-dispersion comprises two different drop size distributions: (1) a small droplet size distribution, and (2) a large droplet size distribution;

wherein the small droplet size distribution is chosen to provide optimum neutralization of the toxic material, and the large droplet size distribution is chosen to hasten the fallout of the small droplets;

wherein generating the co-dispersion of the two different droplet size distributions comprises spraying the DF-200 formulation through two different size spray nozzles that are positioned side-by-side;

wherein the small droplet size distribution has a mean size that ranges from 1 to 20 microns; and wherein the large droplet size distribution has a mean size that ranges from 10 to 100 microns;

wherein the concentration of DF-200 sprayed into the toxic cloud is about 50 to 150 $g/m^3$;

wherein the DF-200 droplets are sprayed from an electrostatic induction spray nozzle operating with an applied voltage of about 1500 to 2000 Volts; with an air pressure of about 80 to 100 psi, and with a DF-200 liquid flow rate of about 200 to 250 mL/minute (per nozzle);

wherein the DF-200 decontamination formulation has a pH value between about 9.6 and 9.8;

wherein the cationic surfactant in the DF-200 formulation comprises a quaternary ammonium salt selected from the group consisting of cetyltrimethyl ammonium bromide, benzalkonium chloride, benzethonium chloride, cetylpyridinium chloride, alkyldimethylbenzylammonium salt, tetrabutyl ammonium bromide, and a mixture of benzyl (C12-C16) alkyldimethylammonium chlorides, and combinations thereof;

wherein the ratio of the concentration of sprayed droplets of DF-200 aqueous decontamination formulation ($g/m^3$) to the concentration of the toxic material in the toxic cloud ($g/m^3$) is at least 40:1;

wherein the DF-200 aqueous decontamination formulation comprises:

2-6% cationic surfactant,
2-6% sodium bicarbonate,
1-4% sodium carbonate,
1-10% propylene glycol,
1-5% silicone polyether liquid,
0.1-2% KOH,
1-5% diacetin,
1-8% hydrogen peroxide, and
remainder water;

wherein the cationic surfactant comprises a mix of alkyl dimethyl benzyl ammonium chlorides and alkyl dimethyl ethylbenzyl ammonium chlorides.

31. A method of decontaminating a cloud of toxic material, comprising:

generating, with a single nozzle, negatively-charged droplets of DF-200 aqueous decontamination formulation; and contacting and chemically reacting the DF-200 droplets with the cloud of toxic material to neutralize and render the toxic cloud harmless;

wherein the DF-200 aqueous decontamination formulation comprises:

a solubilizing agent selected from the group consisting of a cationic surfactant, a cationic hydrotrope, and a fatty alcohol;

a reactive compound selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;

a bleaching activator selected from the group consisting of O-acetyl, N-acetyl, and nitrile group bleaching activators; and water; and wherein generating the droplets comprises spraying the DF-200 formulation through said single nozzle at a high pressure, to generate droplets having a small droplet size distribution; and wherein generating the droplets also comprises spraying the DF-200 formulation through the same said single nozzle at a low pressure, to generate droplets having a large droplet size distribution; and wherein the small droplet size distribution is chosen to provide optimum neutralization of the toxic material, and the large droplet size distribution is chosen to hasten the fallout of the small droplets;

wherein the small droplet size distribution has a mean size that ranges from 1 to 20 microns; and wherein the large droplet size distribution has a mean size that ranges from 10 to 100 microns;

wherein the concentration of DF-200 sprayed into the toxic cloud is about 50 to 150 $g/m^3$;

wherein the DF-200 droplets are sprayed from an electrostatic induction spray nozzle operating with an applied voltage of about 1500 to 2000 Volts; with an air pressure of about 80 to 100 psi, and with a DF-200 liquid flow rate of about 200 to 250 mL/minute (per nozzle);

wherein the DF-200 decontamination formulation has a pH value between about 9.6 and 9.8;

wherein the cationic surfactant in the DF-200 formulation comprises a quaternary ammonium salt selected from the group consisting of cetyltrimethyl ammonium bromide, benzalkonium chloride, benzethonium chloride, cetylpyridinium chloride, alkyldimethylbenzylammonium salt, tetrabutyl ammonium bromide, and a mixture of benzyl (C12-C16) alkyldimethylammonium chlorides, and combinations thereof;

wherein the ratio of the concentration of sprayed droplets of DF-200 aqueous decontamination formulation ($g/m^3$) to the concentration of the toxic material in the toxic cloud ($g/m^3$) is at least 40:1;

wherein the DF-200 aqueous decontamination formulation comprises:

2-6% cationic surfactant,
2-6% sodium bicarbonate,
1-4% sodium carbonate,
1-10% propylene glycol,
1-5% silicone polyether liquid,
0.1-2% KOH,
1-5% diacetin,
1-8% hydrogen peroxide, and
remainder water;

wherein the cationic surfactant comprises a mix of alkyl dimethyl benzyl ammonium chlorides and alkyl dimethyl ethylbenzyl ammonium chlorides.

* * * * *